(12) United States Patent
Nierenberg et al.

(10) Patent No.: US 10,022,091 B2
(45) Date of Patent: *Jul. 17, 2018

(54) USER INTERFACE FOR ARTIFACT REMOVAL IN AN EEG

(71) Applicant: Persyst Development Corporation, San Diego, CA (US)

(72) Inventors: Nicolas Nierenberg, La Jolla, CA (US); Scott B. Wilson, Del Mar, CA (US); Mark L. Scheuer, Wexford, PA (US)

(73) Assignee: Persyst Development Corporation, Solana Beach, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 14/991,928

(22) Filed: Jan. 9, 2016

(65) Prior Publication Data

US 2016/0120478 A1    May 5, 2016

Related U.S. Application Data

(63) Continuation of application No. 14/583,677, filed on Dec. 27, 2014, now Pat. No. 9,232,922, which is a continuation of application No. 13/684,469, filed on Nov. 23, 2012, now Pat. No. 9,055,927, which is a continuation-in-part of application No. 13/620,784, filed on Sep. 15, 2012, now Pat. No. 8,666,484, and a continuation-in-part of application No. 13/542,665, filed on Jul. 6, 2012, now abandoned.

(60) Provisional application No. 61/563,839, filed on Nov. 28, 2011, provisional application No. 61/563,731, filed on Nov. 25, 2011.

(51) Int. Cl.
| | |
|---|---|
| A61B 5/04 | (2006.01) |
| A61B 5/00 | (2006.01) |
| A61B 5/0476 | (2006.01) |
| A61B 5/0478 | (2006.01) |
| G16H 40/63 | (2018.01) |

(52) U.S. Cl.
CPC ........ *A61B 5/7207* (2013.01); *A61B 5/04012* (2013.01); *A61B 5/04017* (2013.01); *A61B 5/0476* (2013.01); *A61B 5/0478* (2013.01); *A61B 5/7203* (2013.01); *A61B 5/725* (2013.01); *A61B 5/7246* (2013.01); *A61B 5/742* (2013.01); *A61B 5/743* (2013.01); *A61B 5/7425* (2013.01); *A61B 5/7475* (2013.01); *G16H 40/63* (2018.01)

(58) Field of Classification Search
None
See application file for complete search history.

(56) References Cited

U.S. PATENT DOCUMENTS 5,520,191 A * 5/1996 Karlsson ............... A61B 5/0006
600/512
6,602,202 B2 * 8/2003 John ................... A61B 5/04845
600/544

(Continued)

*Primary Examiner* — Etsub Berhanu
(74) *Attorney, Agent, or Firm* — Clause Eight IPS; Michael Catania

(57) ABSTRACT

A method and system for a user interface for artifact removal in an EEG is disclosed herein. The invention allows an operator to select a plurality of artifacts to be automatically removed from an EEG recording using a user interface. The operator pushes a button on the user interface to apply a plurality of filters to remove the plurality of artifacts from the EEG and generate a clean EEG for viewing.

7 Claims, 36 Drawing Sheets

(56) References Cited

U.S. PATENT DOCUMENTS

| | | | | |
|---|---|---|---|---|
| 7,460,905 B2* | 12/2008 | Mase | ............... | A61B 1/0005 |
| | | | | 600/544 |
| 2003/0144600 A1* | 7/2003 | Yarita | ............... | A61B 5/02125 |
| | | | | 600/544 |
| 2004/0059215 A1* | 3/2004 | Nishimura | ............... | A61B 5/00 |
| | | | | 600/410 |
| 2008/0262367 A1* | 10/2008 | Mugler | ............... | A61B 5/0452 |
| | | | | 600/523 |
| 2009/0264786 A1* | 10/2009 | Jacquin | ............... | A61B 5/04012 |
| | | | | 600/544 |
| 2012/0101401 A1* | 4/2012 | Faul | ............... | A61B 5/0476 |
| | | | | 600/544 |

\* cited by examiner

USER INTERFACE FOR ARTIFACT REMOVAL IN AN EEG

CROSS REFERENCES TO RELATED APPLICATIONS

The Present Application is a continuation application of U.S. patent application Ser. No. 14/583677, filed on Dec. 27, 2014, which is a continuation application of U.S. patent application Ser. No. 13/684469, filed on Nov. 23, 2012, now U.S. Pat. No. 9,055,927, issued on Jun. 16, 2015, which claims priority to U.S. Provisional Patent Application No. 61/563839, filed on Nov. 28, 2011, now abandoned, U.S. patent application Ser. No. 13/684469 is also a continuation-in-part application of U.S. patent application Ser. No. 13/620784, filed on Sep. 15, 2012, now U.S. Pat. No. 8,666,484, issued on Mar. 4, 2014, which claims priority to U.S. Provisional Patent Application No. 61/563731, filed on Nov. 25, 2011, now abandoned, and U.S. patent application Ser. No. 13/684469 is also a continuation-in-part application of U.S. patent application Ser. No. 13/542665, filed on Jul. 6, 2012, now abandoned, all of which are hereby incorporated by reference in their entireties.

STATEMENT REGARDING FEDERALLY SPONSORED RESEARCH OR DEVELOPMENT

Not Applicable

BACKGROUND OF THE INVENTION

Field of the Invention

The present invention generally relates to a method and system for displaying EEG data. More specifically, the present invention relates to analyzing an EEG recording.

Description of the Related Art

An electroencephalogram ("EEG") is a diagnostic tool that measures and records the electrical activity of a person's brain in order to evaluate cerebral functions. Multiple electrodes are attached to a person's head and connected to a machine by wires. The machine amplifies the signals and records the electrical activity of a person's brain. The electrical activity is produced by the summation of neural activity across a plurality of neurons. These neurons generate small electric voltage fields. The aggregate of these small electric voltage fields create an electrical reading which electrodes on the person's head are able to detect and record. An EEG is a superposition of multiple simpler signals. In a normal adult, the amplitude of an EEG signal typically ranges from 1 micro-Volt to 100 micro-Volts, and the EEG signal is approximately 10 to 20 milli-Volts when measured with subdural electrodes. The monitoring of the amplitude and temporal dynamics of the electrical signals provides information about the underlying neural activity and medical conditions of the person.

An EEG is performed to: diagnose epilepsy; verify problems with loss of consciousness or dementia; verify brain activity for a person in a coma; study sleep disorders, monitor brain activity during surgery, and additional physical problems.

Multiple electrodes (typically 17-21, however there are standard positions for at least 70) are attached to a person's head during an EEG. The electrodes are referenced by the position of the electrode in relation to a lobe or area of a person's brain. The references are as follows: F=frontal; Fp=frontopolar; T=temporal; C=central; P=parietal; O=occipital; and A=auricular (ear electrode). Numerals are used to further narrow the position and "z" points relate to electrode sites in the midline of a person's head. An electrocardiogram ("EKG") may also appear on an EEG display.

The EEG records brain waves from different amplifiers using various combinations of electrodes called montages. Montages are generally created to provide a clear picture of the spatial distribution of the EEG across the cortex. A montage is an electrical map obtained from a spatial array of recording electrodes and preferably refers to a particular combination of electrodes examined at a particular point in time.

In bipolar montages, consecutive pairs of electrodes are linked by connecting the electrode input 2 of one channel to input 1 of the subsequent channel, so that adjacent channels have one electrode in common. The bipolar chains of electrodes may be connected going from front to back (longitudinal) or from left to right (transverse). In a bipolar montage signals between two active electrode sites are compared resulting in the difference in activity recorded. Another type of montage is the referential montage or monopolar montage. In a referential montage, various electrodes are connected to input 1 of each amplifier and a reference electrode is connected to input 2 of each amplifier. In a reference montage, signals are collected at an active electrode site and compared to a common reference electrode.

Reference montages are good for determining the true amplitude and morphology of a waveform. For temporal electrodes, CZ is usually a good scalp reference.

Being able to locate the origin of electrical activity ("localization") is critical to being able to analyze the EEG. Localization of normal or abnormal brain waves in bipolar montages is usually accomplished by identifying "phase reversal," a deflection of the two channels within a chain pointing to opposite directions. In a referential montage, all channels may show deflections in the same direction. If the electrical activity at the active electrodes is positive when compared to the activity at the reference electrode, the deflection will be downward. Electrodes where the electrical activity is the same as at the reference electrode will not show any deflection. In general, the electrode with the largest upward deflection represents the maximum negative activity in a referential montage.

Some patterns indicate a tendency toward seizures in a person. A physician may refer to these waves as "epileptiform abnormalities" or "epilepsy waves." These include spikes, sharp waves, and spike-and-wave discharges. Spikes and sharp waves in a specific area of the brain, such as the left temporal lobe, indicate that partial seizures might possibly come from that area. Primary generalized epilepsy, on the other hand, is suggested by spike-and-wave discharges that are widely spread over both hemispheres of the brain, especially if they begin in both hemispheres at the same time.

There are several types of brain waves: alpha waves, beta waves, delta wave, theta waves and gamma waves. Alpha waves have a frequency of 8 to 12 Hertz ("Hz"). Alpha waves are normally found when a person is relaxed or in a waking state when a person's eyes are closed but the person is mentally alert. Alpha waves cease when a person's eyes are open or the person is concentrating. Beta waves have a frequency of 13 Hz to 30 Hz. Beta waves are normally found when a person is alert, thinking, agitated, or has taken high doses of certain medicines. Delta waves have a frequency of less than 3 Hz. Delta waves are normally found only when a person is asleep (non-REM or dreamless sleep) or the person is a young child. Theta waves have a frequency of 4

Hz to 7 Hz. Theta waves are normally found only when the person is asleep (dream or REM sleep) or the person is a young child. Gamma waves have a frequency of 30 Hz to 100 Hz. Gamma waves are normally found during higher mental activity and motor functions.

The following definitions are used herein.

"Amplitude" refers to the vertical distance measured from the trough to the maximal peak (negative or positive). It expresses information about the size of the neuron population and its activation synchrony during the component generation.

The term "analogue to digital conversion" refers to when an analogue signal is converted into a digital signal which can then be stored in a computer for further processing. Analogue signals are "real world" signals (e.g., physiological signals such as electroencephalogram, electrocardiogram or electrooculogram). In order for them to be stored and manipulated by a computer, these signals must be converted into a discrete digital form the computer can understand.

"Artifacts" are electrical signals detected along the scalp by an EEG, but that originate from non-cerebral origin. There are patient related artifacts (e.g., movement, sweating, ECG, eye movements) and technical artifacts (50/60 Hz artifact, cable movements, electrode paste-related).

The term "differential amplifier" refers to the key to electrophysiological equipment. It magnifies the difference between two inputs (one amplifier per pair of electrodes).

"Duration" is the time interval from the beginning of the voltage change to its return to the baseline. It is also a measurement of the synchronous activation of neurons involved in the component generation.

"Electrode" refers to a conductor used to establish electrical contact with a nonmetallic part of a circuit. EEG electrodes are small metal discs usually made of stainless steel, tin, gold or silver covered with a silver chloride coating. They are placed on the scalp in special positions.

"Electrode gel" acts as a malleable extension of the electrode, so that the movement of the electrodes leads is less likely to produce artifacts. The gel maximizes skin contact and allows for a low-resistance recording through the skin.

The term "electrode positioning" (10/20 system) refers to the standardized placement of scalp electrodes for a classical EEG recording. The essence of this system is the distance in percentages of the 10/20 range between Nasion-Inion and fixed points. These points are marked as the Frontal pole (Fp), Central (C), Parietal (P), occipital (O), and Temporal (T). The midline electrodes are marked with a subscript z, which stands for zero. The odd numbers are used as subscript for points over the left hemisphere, and even numbers over the right "Electroencephalogram" or "EEG" refers to the tracing of brain waves, by recording the electrical activity of the brain from the scalp, made by an electroencephalograph.

"Electroencephalograph" refers to an apparatus for detecting and recording brain waves (also called encephalograph).

"Epileptiform" refers to resembling that of epilepsy.

"Filtering" refers to a process that removes unwanted frequencies from a signal.

"Filters" are devices that alter the frequency composition of the signal.

"Montage" means the placement of the electrodes. The EEG can be monitored with either a bipolar montage or a referential one. Bipolar means that there are two electrodes per one channel, so there is a reference electrode for each channel. The referential montage means that there is a common reference electrode for all the channels.

"Morphology" refers to the shape of the waveform. The shape of a wave or an EEG pattern is determined by the frequencies that combine to make up the waveform and by their phase and voltage relationships. Wave patterns can be described as being: "Monomorphic". Distinct EEG activity appearing to be composed of one dominant activity. "Polymorphic". distinct EEG activity composed of multiple frequencies that combine to form a complex waveform. "Sinusoidal". Waves resembling sine waves. Monomorphic activity usually is sinusoidal. "Transient". An isolated wave or pattern that is distinctly different from background activity.

"Spike" refers to a transient with a pointed peak and a duration from 20 to under 70 msec.

The term "sharp wave" refers to a transient with a pointed peak and duration of 70-200 msec.

The term "neural network algorithms" refers to algorithms that identify sharp transients that have a high probability of being epileptiform abnormalities.

"Noise" refers to any unwanted signal that modifies the desired signal. It can have multiple sources.

"Periodicity" refers to the distribution of patterns or elements in time (e.g., the appearance of a particular EEG activity at more or less regular intervals). The activity may be generalized, focal or lateralized.

An EEG epoch is an amplitude of a EEG signal as a function of time and frequency.

Various techniques have been developed to present the EEG data to a physician or technician. However, these techniques are still lacking. Learning what is an artifact and how to see what is in the underlying signal is one of the most difficult problems in EEG interpretation. A number of techniques have been developed for algorithmically removing artifact to produce a cleaner EEG, but in order for these to be adopted commercially it is necessary to develop a user interface that allows the user to see how the original signal has evolved to the clean signal.

BRIEF SUMMARY OF THE INVENTION

The present invention provides a solution to this problem by providing a user interface for artifact removal in an EEG. This is important for two main reasons. First it provides confidence to the user that the cleaner EEG correctly represents what would be present in the absence of artifact. Secondly the user may want to see the original signal, or the signal after only partial cleaning in order to determine if there is information present that is useful.

In the present invention a process of producing a "clean" EEG involves a series of steps. For example artifacts related to electrical issues might be one step. Another step would remove eye blinks. Another step might remove surface muscle. Yet another step might remove effects of tongue movement. Each step is a kind of algorithmic filter, although this is very different than the classic filters that remove everything within a certain frequency range. Currently EEG is typically displayed as a series of traces organized by channel. Channels commonly represent the voltage difference between two scalp electrodes, but they can also represent the differences between an electrode and an average or other aggregation of a group of electrodes. The traces have a vertical axis of voltage and a horizontal axis of time. Sets of channels are displayed on a page, and a set of channels is called a montage.

The information displayed in a montage can commonly be filtered by removing certain frequency ranges. There are also frequently other options such as limiting "pen deflection" which limits the amplitude of a trace and drawing a horizontal line until the amplitude is below the limit.

With the introduction of artifact filters the user will need the ability to select which artifact filters are being applied and have that confirmed on the display. In addition they will need the ability to simultaneously show a set of traces for each channel representing the effects of the artifact filters. One choice would be to show both the original signal as well as the signal after applying the entire set of selected filters. They may also want to see a trace with the difference between the original signal and the filtered signal. They may also want to see traces showing the signal at different points in the process of artifact filtering. For example they might want to see a trace with just the muscle artifacts removed but leaving the eye blinks. In order to remove some artifacts like eye blinks the software might use specific recognition algorithms that detect the pattern. In this case the user may simply want to see an indication that an eye blink or other pattern was present while still removing the effects of the pattern from the trace. (People reading EEGs use eye blinks as one way to tell that the patient is awake, but the eye blink produces a large artifact obscuring other information on the channels it affects).

Another feature of the present invention is the ability to select colors for the various traces and the amount of darkness/emphasis. Some users may want the original signal to be primary with the artifact filtered traces present in the background as reference. Other users may want one of the filtered traces to be primary. Choice of colors is important for this reason and also because a significant fraction of people are color blind to certain colors.

Another aspect of the artifact filtering process is that it will break the signal into a set of underlying signals. This can be useful even after artifacts are removed in seeing the various components of the true signal from the brain. For example there might be slow waves separate from individual epileptiform patterns. A user might want to choose to see these components separately on a channel to make it easier to see the various portions of the true signal. Doing this would likely not have been useful prior to removing most significant artifacts.

Another aspect of the present invention is a single "button" that applies a set of pre-selected artifact filters in a standard program used to review EEG. The button allows a technician to toggle on and off to allow for filtered and unfiltered traces for review by the technician.

One aspect of the present invention is a method for analyzing an EEG recording. The method includes generating an EEG recording from a machine comprising a plurality of electrodes, an amplifier and processor. The method also includes processing the EEG to create a processed EEG recording for analysis. The method also includes recognizing a pattern in the processed EEG recording.

Another aspect of the present invention is a system for analyzing an EEG recording. The system includes electrodes for generating a plurality of EEG signals, at least one amplifier connected to each of the plurality of electrodes by a plurality of wires to amplify each of the plurality of EEG signals, a processor connected to the amplifier to generate an EEG recording from the plurality of EEG signals, a display connected to the processor for displaying an EEG recording. The processor is configured to recognize a pattern in the processed EEG recording.

Yet another aspect of the present invention is a method for analyzing an EEG recording. The method includes generating an EEG recording from a machine comprising a plurality of electrodes, an amplifier and processor. The method also includes processing the EEG to create a processed EEG recording for analysis. The method also includes detecting a plurality of events in the processed EEG recording. The method also includes presenting the plurality of events as an event density graph.

Another aspect of the present provides an EEG system and method that overlays a processed EEG report over a raw EEG report to permit a physician or technician to clearly see the activity reported.

This embodiment provides the ability to select short overlapping epochs where the results of artifact removal from each epoch is stitched together with the result from the next and previous epoch. This stitching can be accomplished many ways, but in a preferred method the signals from the two epochs are combined using a weighted average where the weight is proportional to the ratio of the distance to the epoch centers.

For example an epoch length of two seconds is selected with an increment (epoch step) of one second. Artifact removal using BSS and other techniques is performed on a set of channels for seconds one and two producing a two second length "clean" result. Then artifact removal is performed on seconds two and three producing an overlapping clean result. The results overlap in the second second of the record. For each channel, the weighted average of the two overlapping results produces a final result without discontinuities. In the portion of the second nearer the center of the first epoch the value from the first epoch is weighted higher, and likewise for the portion nearer the center of the second epoch. Those skilled in the pertinent art will recognize that different or variable epoch lengths or steps may be selected while moving through the record. Also a different stitching technique might be used.

One aspect of the present invention is a method for filtering artifacts from an EEG signal. The method includes generating an EEG signal from a machine comprising a plurality of electrodes, an amplifier and processor. The method also includes transforming the EEG signal from a set of channels into a plurality of epochs. Each of the plurality of epochs has an epoch duration length of less than or equal to two seconds and an increment of less than or equal to one second. The method also includes filtering artifacts from each of the plurality of epochs using a blind source separation algorithm to generate a plurality of clean epochs. The method also includes combining the plurality of clean epochs to generate a processed EEG recording.

Yet another aspect of the present invention is a method for filtering artifacts from an EEG signal using a blind source separation algorithm. The method includes generating an EEG signal from a machine comprising a plurality of electrodes, an amplifier and processor. The method also includes transforming the EEG signal from a set of channels into a plurality of epochs. The method also includes filtering artifacts from each of the plurality of epochs using a blind source separation algorithm to generate a plurality of clean epochs. The method also includes combining the plurality of clean epochs to generate a processed EEG recording.

Yet another aspect of the present invention is a system for filtering artifacts from an EEG signal. The system includes electrodes, an amplifier, a processor and a display. The electrodes generate EEG signals. The amplifier is connected to each of the electrodes by wires and amplifies the EEG signals. The processor is connected to the amplifier to generate an EEG recording from the EEG signals. The display is connected to the processor to display an EEG recording. The processor is configured to transform each of the plurality of EEG signals from a set of channels into a plurality of epochs, remove artifacts from each of the plurality of epochs using a blind source separation algorithm to generate a plurality of clean epochs, and combine the plurality of clean epochs to generate a processed EEG recording for display.

Yet another aspect of the present invention is a method for filtering artifacts from an EEG signal using a artifact removal algorithm. The method includes generating an EEG signal from a machine comprising a plurality of electrodes, an amplifier and processor. The method also includes transforming the EEG signal from a set of channels into a plurality of epochs. The method also includes filtering artifacts from each of the plurality of epochs using an artifact removal algorithm to generate a plurality of clean epochs. The method also includes combining the plurality of clean epochs to generate a processed EEG recording.

Yet another aspect of the present invention is a method for filtering artifacts from an EEG signal by selecting an epoch time and increment. The method includes generating an EEG signal for a patient from a machine comprising a plurality of electrodes attached to the patient, an amplifier and processor. The method also includes selecting an epoch time length and an epoch time increment. The method also includes filtering artifacts for each of a plurality of epochs using an artifact removal algorithm to generate a plurality of clean epochs. The method also includes assigning a weighted average to each of the plurality of clean epochs. The method also includes combining the plurality of clean epochs to overlap to generate a processed EEG recording without discontinuities.

Yet another aspect of the present invention is a system for filtering artifacts from an EEG signal. The system includes electrodes, a processor, and a display. The electrodes generate EEG signals. The processor is connected to the electrodes to generate an EEG recording from the EEG signals. The display is connected to the processor and displays an EEG recording. The processor is configured to select an epoch time length and an epoch time increment, filter artifacts for each of a plurality of epochs using an artifact removal algorithm to generate a plurality of clean epochs, assign a weighted average to each of the plurality of clean epochs, and combine the plurality of clean epochs to overlap to generate a processed EEG recording without discontinuities.

Still another aspect of the present invention is a method for displaying EEG data. The method includes generating an original EEG report from an EEG signal. The original EEG report is generated from an EEG machine comprising a plurality of electrodes and processor. The original EEG report comprises a first plurality of channels. The method also includes performing artifact reduction on the original EEG signal to generate a processed EEG report. The processed EEG report comprises a second plurality of channels. The method also includes overlaying the processed EEG report on the original EEG report to generate a combined EEG report. An x-axis of the processed EEG report is aligned with an x-axis of the original EEG report. A y-axis of the processed EEG report is aligned with an y-axis of the original EEG report. The first plurality of channels of the original EEG report are equal to the second plurality of channels of the processed EEG report. The method also includes displaying the combined EEG report wherein the processed EEG report is visually distinctive from the original EEG report. An activity at a specific time on one channel of the first plurality of channels of the original EEG report is identifiable on a corresponding channel of the second plurality of channels of the processed EEG report at the specific time. The activity is preferably spikes, sharp waves, spike and wave discharges, artifacts, and the like.

Still another aspect of the present invention is a method for displaying a combined EEG report. The method includes generating an original EEG report from an EEG signal. The original EEG report is generated from an EEG machine comprising a plurality of electrodes and processor. The original EEG report comprises a first plurality of channels. The method also includes performing artifact reduction on the original EEG signal to generate a processed continuous EEG report. The processed EEG report comprises a second plurality of channels. The method also includes overlaying the processed continuous EEG report on the original EEG report to generate a combined EEG report. An x-axis of the processed continuous EEG report is aligned with an x-axis of the original EEG report. A y-axis of the processed continuous EEG report is aligned with an y-axis of the original EEG report. The first plurality of channels of the original EEG report are equal to the second plurality of channels of the processed continuous EEG report. The method also includes displaying the combined EEG report wherein the processed EEG report is visually distinctive from the original EEG report. An activity at a specific time on one channel of the first plurality of channels of the original EEG report is identifiable on a corresponding channel of the second plurality of channels of the processed continuous EEG report at the specific time.

Still another aspect of the present invention is a system for displaying EEG data. The system includes a patient component, a machine component and a display screen. The patient component comprises a plurality of electrodes for generating an EEG signal. The EEG machine component comprises an amplifier and a processor. The processor is configured to generate an original EEG report from an EEG signal. The original EEG report comprises a first plurality of channels. The processor is also configured to perform artifact reduction on the original EEG signal to generate a processed EEG report. The processed EEG report comprises a second plurality of channels. The processor is also configured to overlay the processed EEG report on the original EEG report to generate a combined EEG report. An x-axis of the processed EEG report is aligned with an x-axis of the original EEG report. A y-axis of the processed EEG report is aligned with an y-axis of the original EEG report. The first plurality of channels of the original EEG report are equal to the second plurality of channels of the processed EEG report. The display screen displays the combined EGG report wherein the processed EEG report is visually distinctive from the original EEG report, and wherein an activity at a specific time on one channel of the first plurality of channels of the original EEG report is identifiable on a corresponding channel of the second plurality of channels of the processed EEG report at the specific time.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
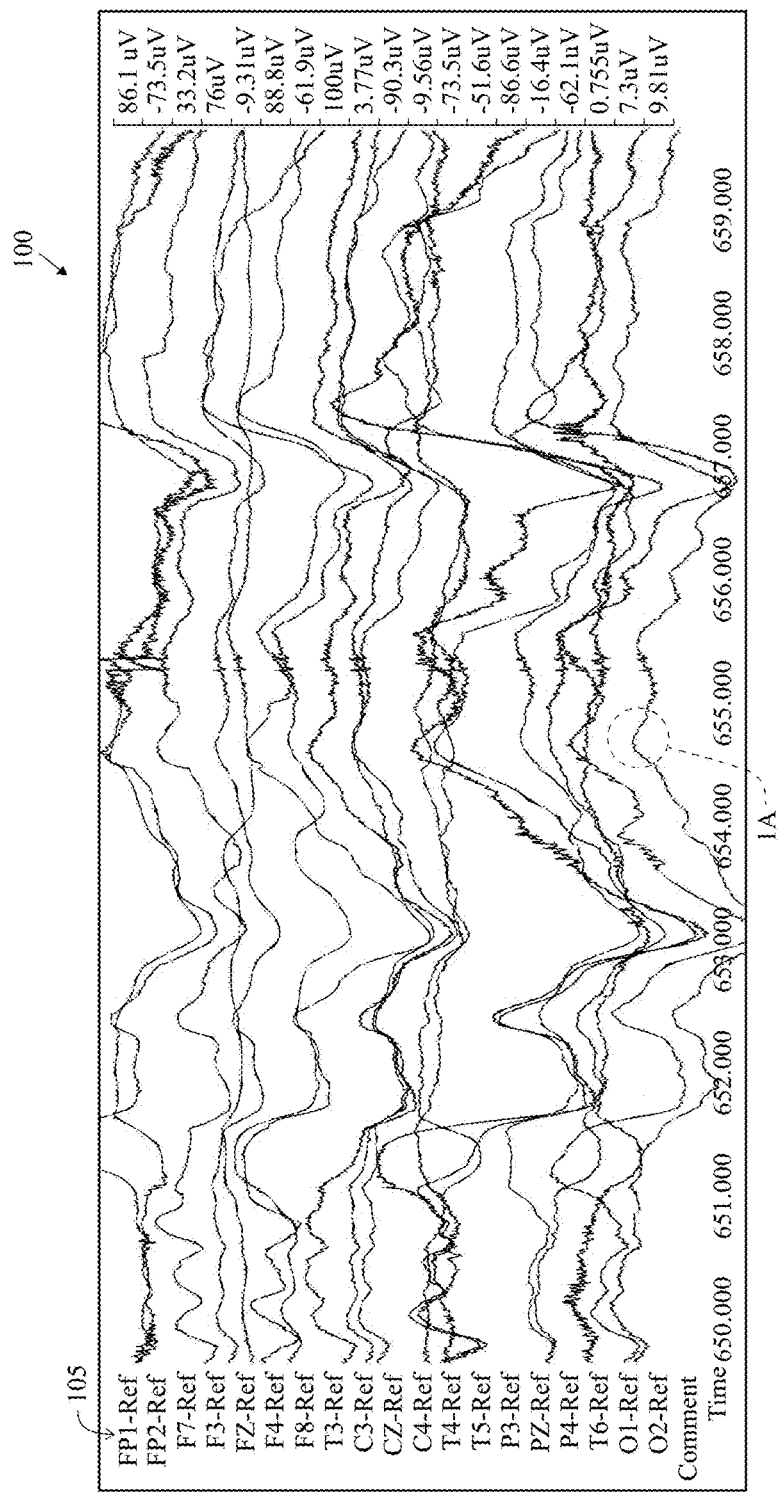
FIG. 1 is an illustration of a portion of a raw EEG report having nineteen channels.
Figure 1A:
FIG. 1A is an enlargement of circle 1A of FIG. 1.

A raw or original EEG report 100 is shown in FIG. 1. The original EEG report 100 has a plurality of channels FP1-Ref through to O2-Ref, shown at the Y axis 105 of the report. The X-axis of the report is time. The original EEG report 100 has not been subjected to artifact reduction. The original EEG report contains artifacts from various sources such as muscle movement, eye movement, sweating, electrode cables and the like. However, the EEG may also have certain activity that a physician or technician is looking for from the EEG report in order to accurately analyze the patient's brain activity. For example, the activity shown in FIG. 1A at a time 655.000 may represent a certain stage of brain activity for the patient that is important to the physician or technician. However, normally, the physician or technician will not review the raw EEG report 100 due to the presence of artifacts.

Figure 2:
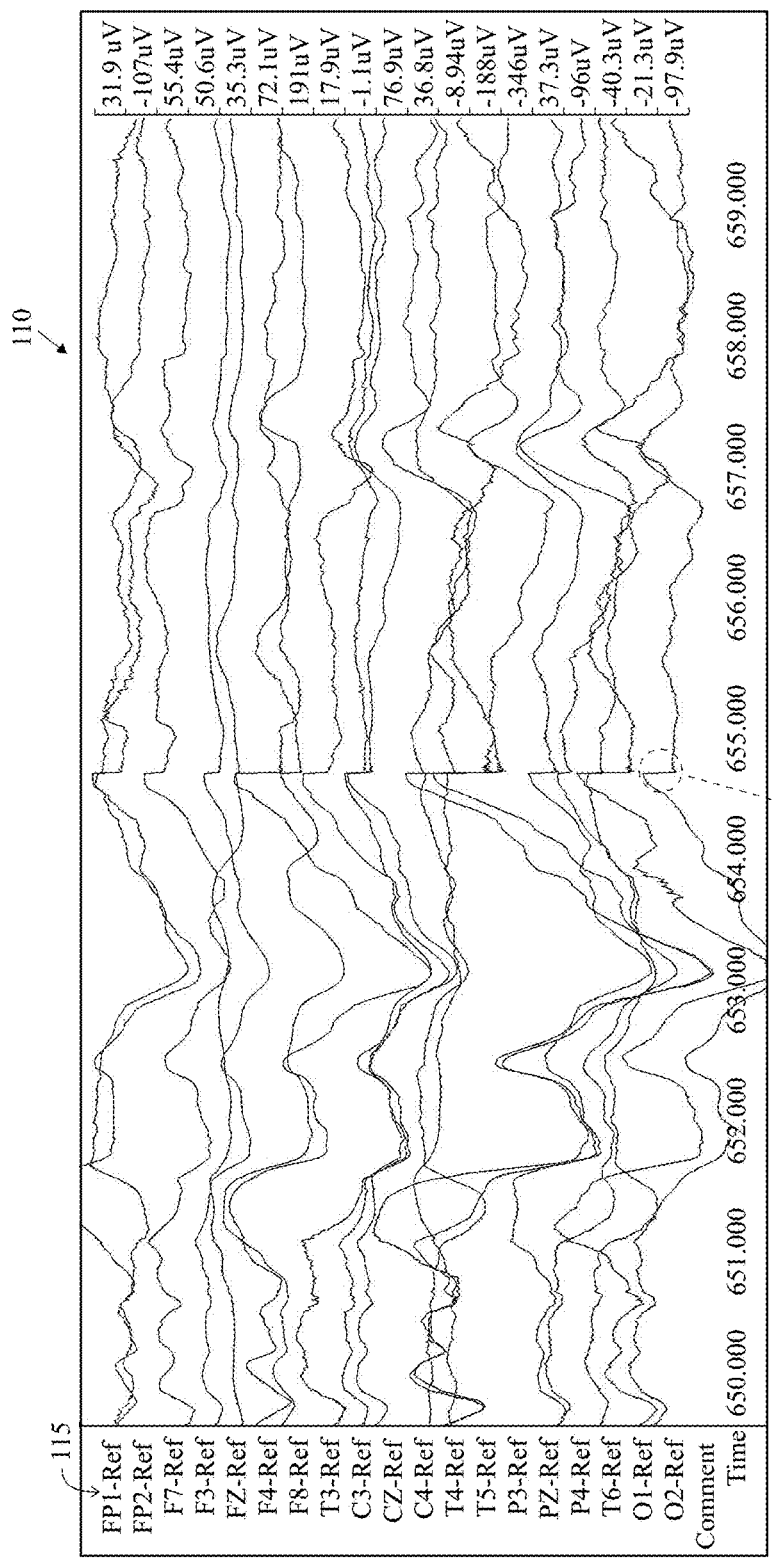
FIG. 2 is an illustration of a portion of a processed EEG report having nineteen channels in which epochs do not overlap.
Figure 2A:
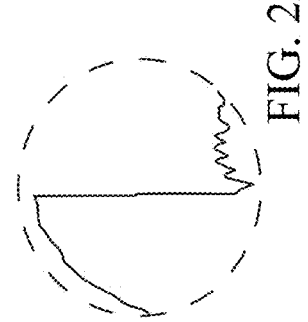
FIG. 2A is an enlargement of circle 2A of FIG. 2.

FIG. 2 is an illustration of a processed EEG report 110 of the original EEG report 100 of FIG. 1 that has undergone artifact reduction and the stitching of epochs in order to recreate the EEG report. The processed EEG report 110 has a plurality of channels FP1-Ref through to O2-Ref, shown at the Y axis 115 of the report. The X-axis of the report is time. As shown in FIG. 2A, the processed EEG report 110 at time 655.000 is quite different in appearance than the original EEG report 100 at time 655.000. This is primarily due to stitching of epochs to recreate the EEG report, however, if a physician or technician were only looking at the processed EEG report 110, the physician or technician would not be aware of the true activity at time 655.000.

Figure 3:
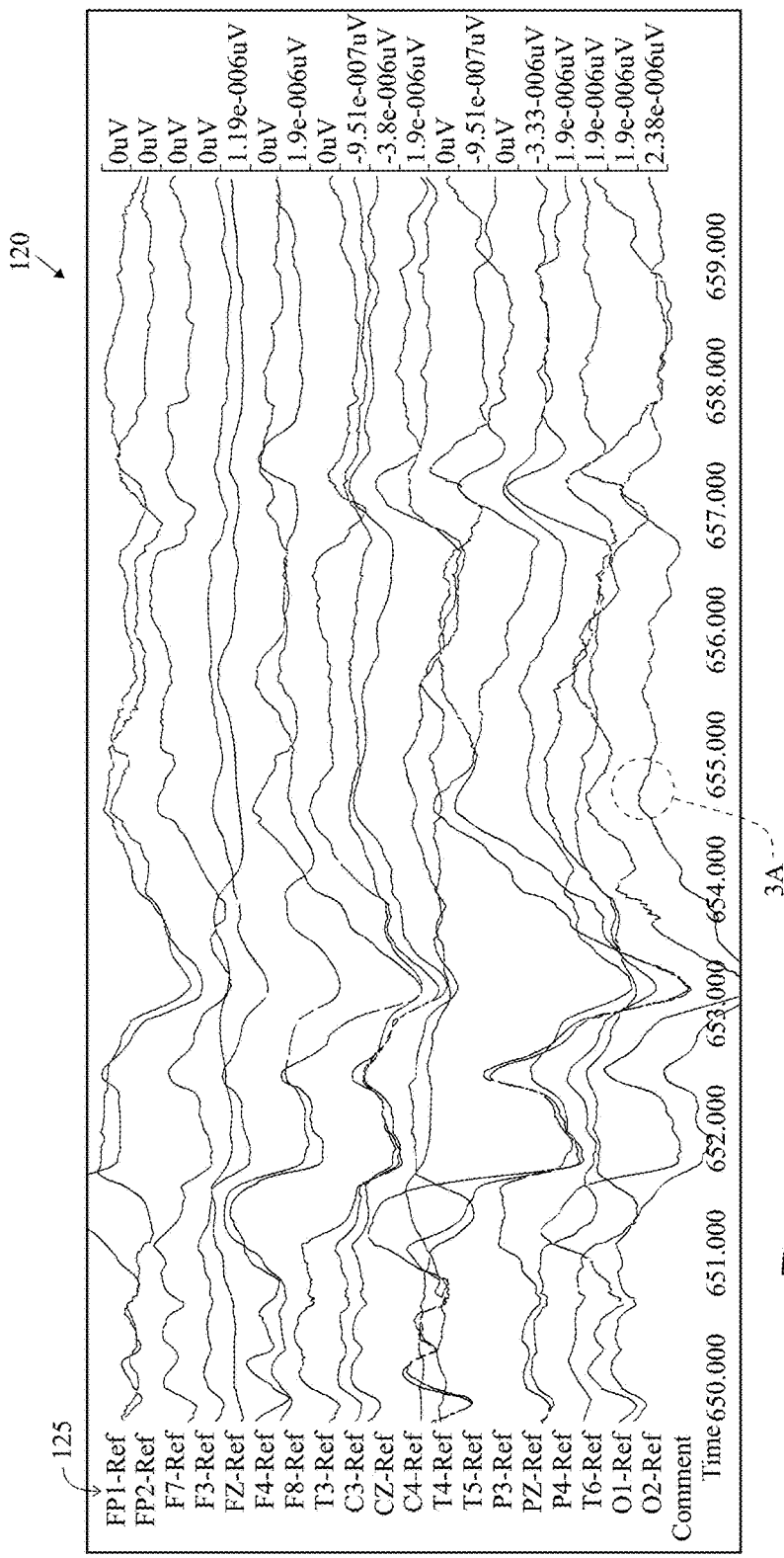
FIG. 3 is an illustration of a portion of a processed continuous EEG report in which sections of the epochs of the EEG report are stitched to overlap.
Figure 3A:
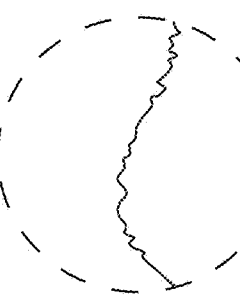
FIG. 3A is an enlargement of circle 3A of FIG. 3.

FIG. 3 is an illustration of a processed continuous EEG report 120 of the original EEG report 100 of FIG. 1 that has undergone artifact reduction and the stitching of overlapping epochs in order to recreate the EEG report. The processed EEG report 120 has a plurality of channels FP1-Ref through to O2-Ref, shown at the Y axis 125 of the report. The X-axis of the report is time. As shown in FIG. 3A, the processed EEG report 120 at time 655.000 is more similar in appearance to the original EEG report 100 at time 655.000 than the processed EEG report 110 of FIG. 2. However, there is still difficulty in analyzing a patient's brain activity by switching back and forth from an original EEG report 100 to a processed EEG report 110 or a processed continuous EEG report 120.

Figure 4:
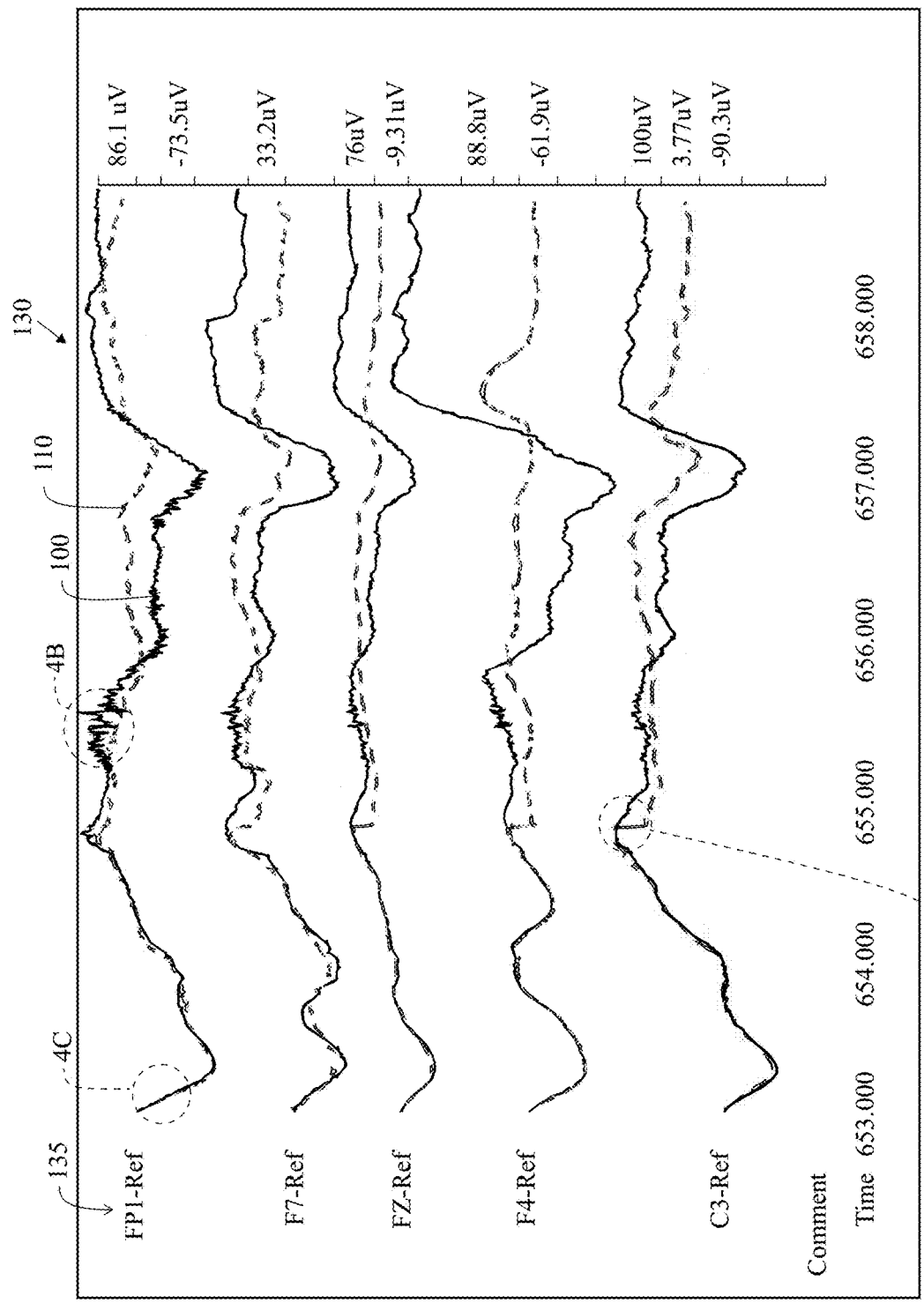
FIG. 4 is an illustration of a portion of a combined EEG report having a processed EEG report overlay on a raw EEG report.

FIG. 4 is an illustration of a combined EEG report 130 comprising the original EEG report 100 and the processed EEG report 110. The illustration of the combined EEG report 130 only has five channels in order to clearly illustrate the invention, however, those skilled in the pertinent art will recognize that the combined EEG report 130 could have sixteen, twenty, twenty-seven or any number of channels without departing from the scope and spirit of the present invention.

As shown in FIGS. 4, 4A, 4B and 4C, the original EEG report 100 has a first line style and the processed EEG report 110 has a second line style distinctive from the first line style in order to allow a physician and technician to easily and visually distinguish between the original EEG report 100 and the processed EEG report 110. In an alternative embodiment, the original EEG report 100 has a first color (e.g., blue) and the processed EEG report 200 has a second color (e.g. red) distinctive from the first color in order to allow a physician and technician to easily and visually distinguish between the original EEG report 100 and the processed EEG report 110.

Figure 4A:
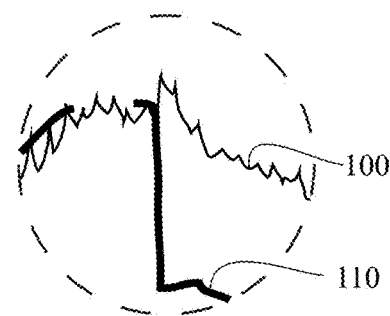
FIG. 4A is an enlargement of circle A of FIG. 4.
Figure 4B:
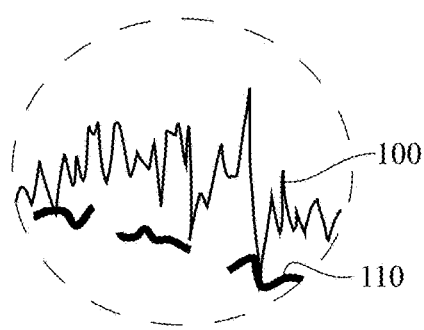
FIG. 4B is an enlargement of circle B of FIG. 4.
Figure 4C:
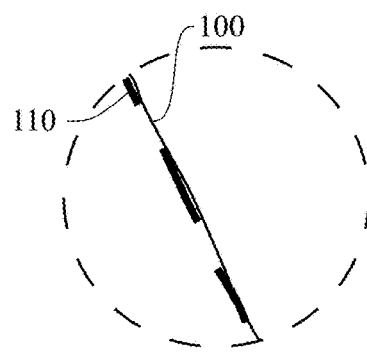
FIG. 4C is an enlargement of circle C of FIG. 4.

As shown in FIG. 4 and specifically FIG. 4C, the channels of the original EEG report 100 are aligned with the channels of the processed EEG report 110 in order to have y-axis 135 alignment.

As shown in FIG. 4 and specifically in FIG. 4A, the x-axis of the original EEG report 100 are aligned with the x-axis of the processed EEG report 110 in order to have time alignment of the two EEG reports in the combined EEG report 130.

Further, the amplitudes for both the original EEG report 100 and the processed EEG report 110 are contained within each of the channels in order to prevent overlapping of the signals.

As shown in FIG. 4B, the original EEG report 100 is quite different from the processed EEG report 110 and a physician or technician may be interested in the activity shown in the original EEG report 100 as compared to the processed EEG report 110.

Those skilled in the pertinent art will recognize that the processed continuous EEG report 120 may be substituted for the processed EEG report 110 in FIG. 4 in order to demonstrate a comparison between the original EEG report 100 and the processed continuous EEG report 120.

Figure 5:
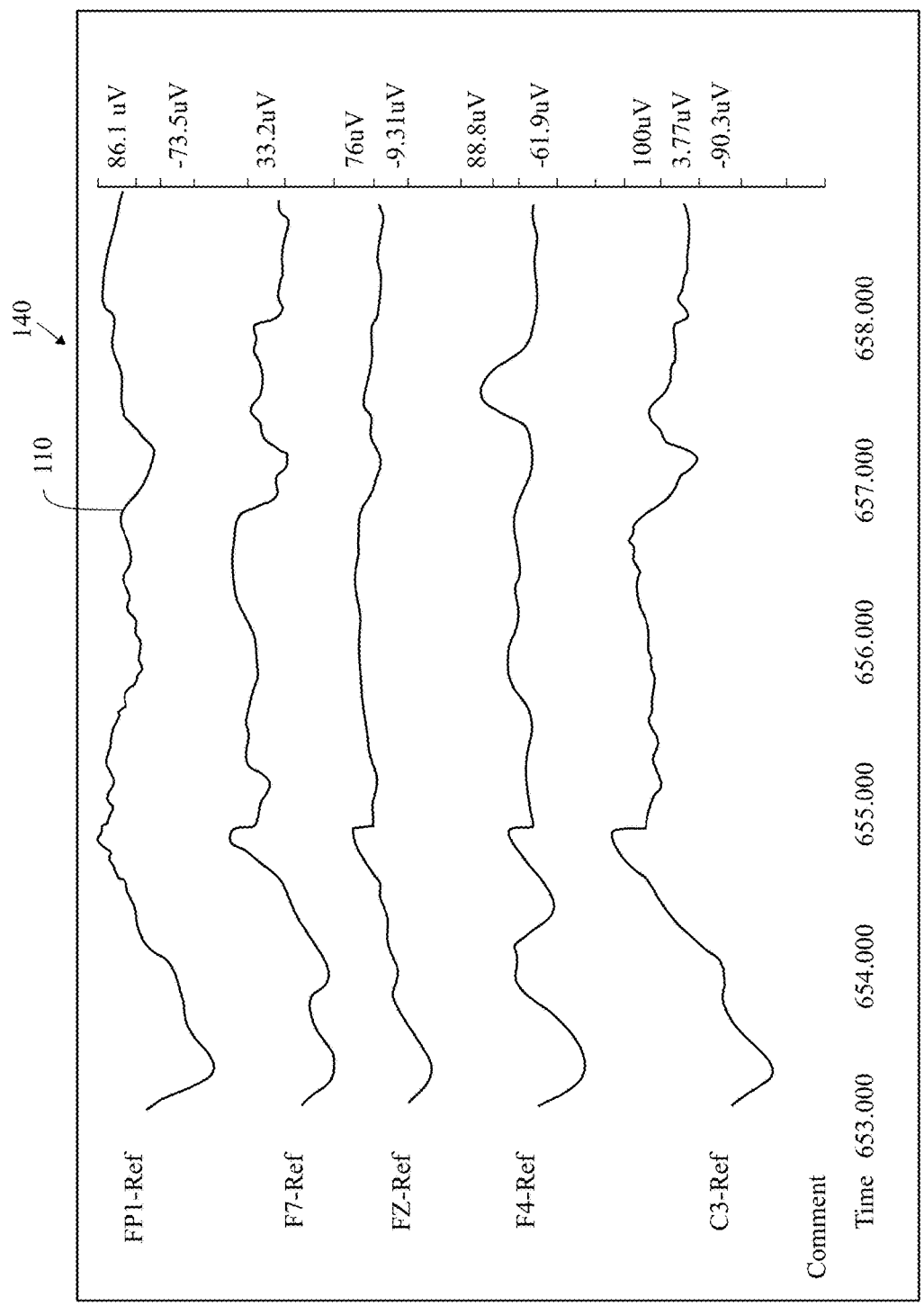
FIG. 5 is an illustration of a portion of processed continuous EEG report in which sections of the epochs of the EEG report are stitched to overlap.

FIG. 5 is an illustration of an EEG report 140, based on the EEG report 120 of FIG. 3, in which channels have been removed for a clearer illustration of channels. The illustration of the combined EEG report 140 only has five channels in order to clearly illustrate the invention, however, those skilled in the pertinent art will recognize that the combined EEG report 140 could have sixteen, twenty, twenty-seven or any number of channels without departing from the scope and spirit of the present invention.

Figure 6:
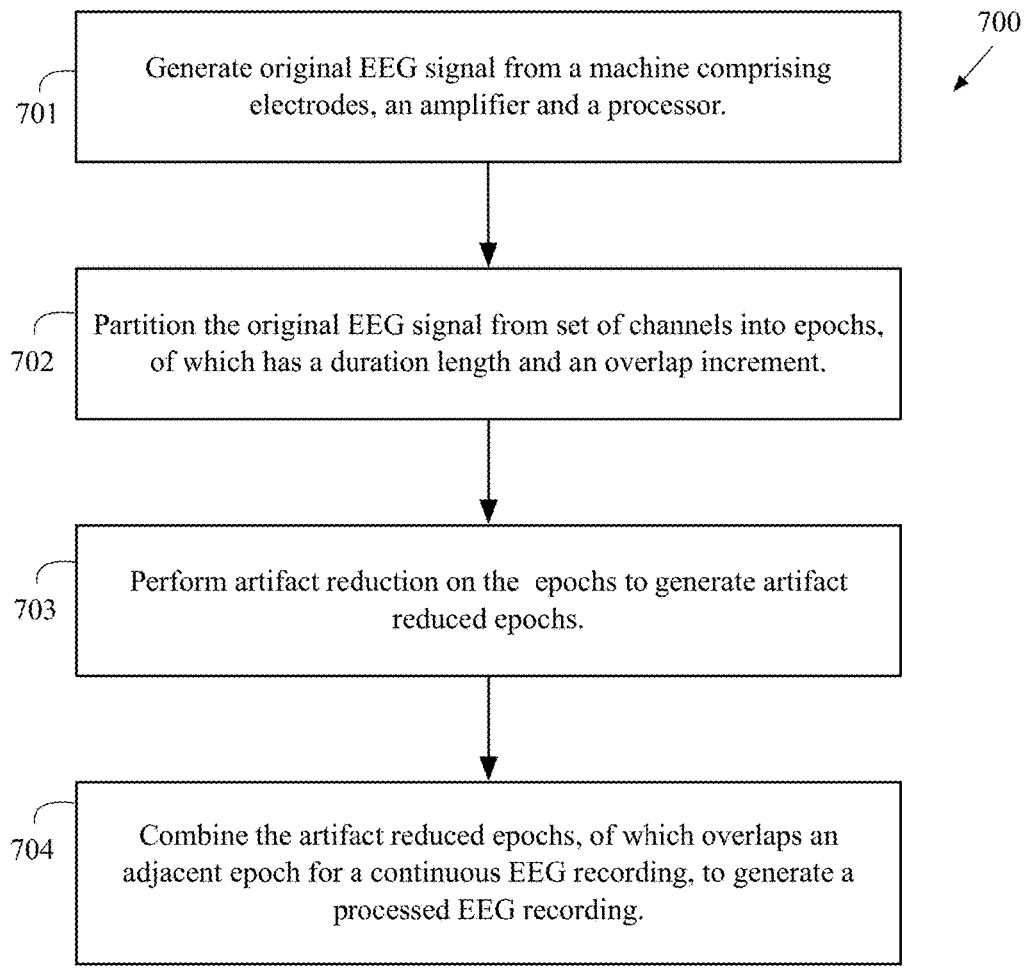
FIG. 6 is a flow chart of a method for displaying EEG data.

A flow chart for a method 700 for displaying EEG data is shown in FIG. 6. At block 701, an original EEG report is generated from an EEG signal. The original EEG report is generated from an EEG machine comprising a plurality of electrodes, an amplifier, and a processor. The original EEG report comprises a first plurality of channels. At block 702, the original EEG signal is partitioned from a set of channels into epochs of which each has a predetermined duration length and an overlap increment. At block 703, artifact reduction is performed on the epochs to generate artifact reduced epochs. At block 704, the artifact reduced epochs are combined with overlapping adjacent epochs for a continuous EEG recording to generate a processed continuous EEG report. The stitched, overlapping epochs and continuous processed EEG report is displayed on a display screen, preferably a monitor. The stitched overlapping epochs and continuous processed EEG report are not missing timeframes from stitching or creating discontinuities in the EEG report, which is read by a physician or technician. All of the brain activity remains since the epochs overlap. The brain activity is preferably spikes, sharp waves, spike and wave discharges, artifacts, and the like.

Figure 7:
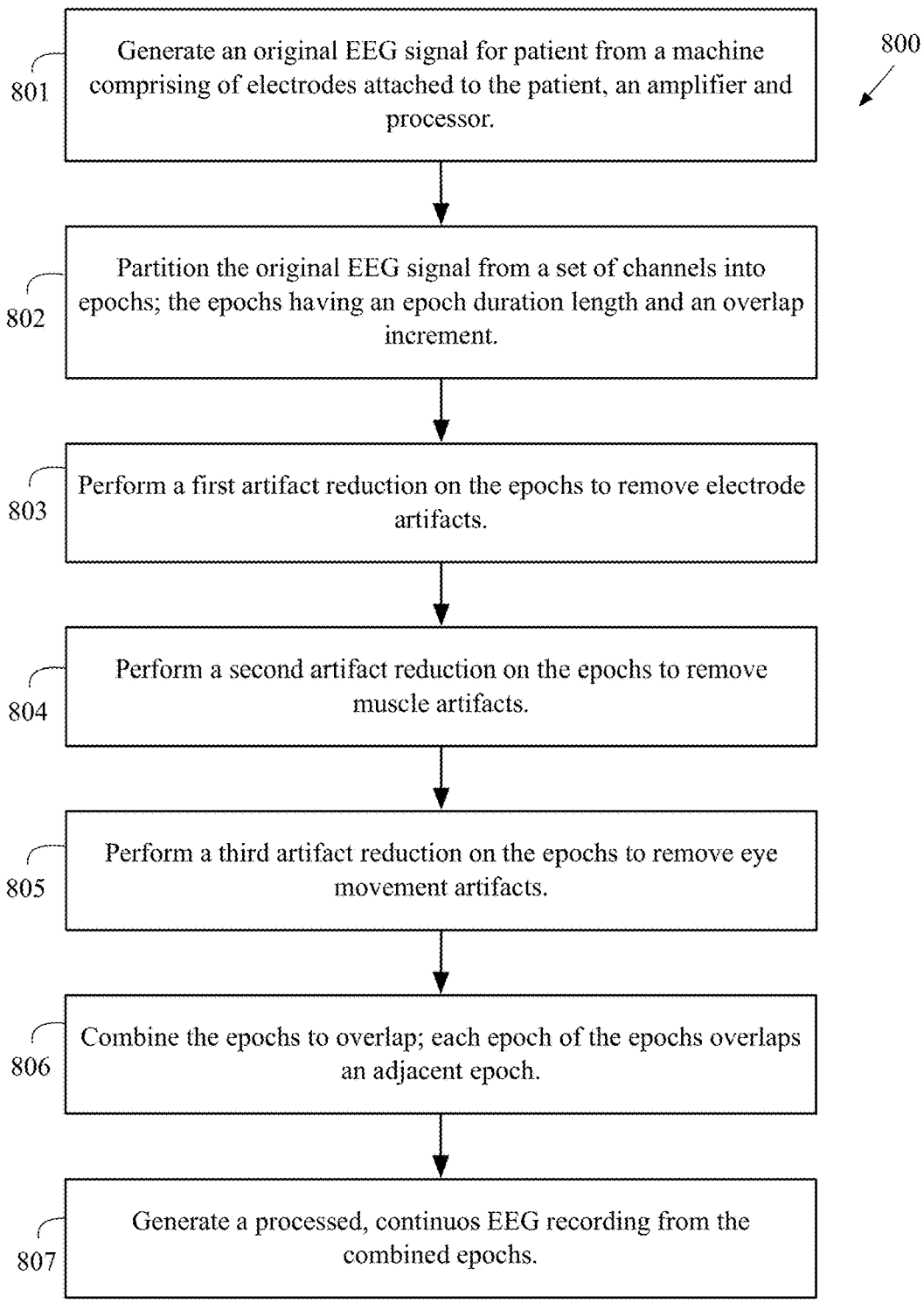
FIG. 7 is a flow chart for a method of artifact reduction.

FIG. 7 is a flow chart of a preferred method 800 for displaying EEG data. At block 801, an original EEG report is generated from an EEG signal for a patient from a machine preferably comprising electrodes attached to the patient, an amplifier and a processor. At block 802, the original EEG signal is partitioned from a set of channels into a plurality of epochs. Each of the plurality of epochs having an epoch duration length and an overlap increment. At block 803, a first artifact reduction is performed on the plurality of epochs to remove electrode artifacts. At block 804, a second artifact reduction is performed on the plurality of epochs to remove muscle artifacts. At block 805, a third artifact reduction is performed on the plurality of epochs to remove eye movement artifacts. At block 806, the plurality of epochs is combined to overlap wherein each epoch of the plurality of epochs overlaps an adjacent epoch to form a processed continuous EEG report. At block 807, a processed continuous EEG recording is generated from the combined epochs.

Each of the plurality of epochs preferably has an epoch duration length of two seconds and an increment of one second. Alternatively, each of the plurality of epochs has an epoch duration length of four seconds and an increment of two seconds. The artifact removal algorithm is preferably a blind source separation algorithm. The blind source separation algorithm is preferably a CCA algorithm or an ICA algorithm. The clean epochs are preferably combined using a weighted average and the weight of the weighted average is preferably proportional to the ratio of the distance to an epoch center.

Figure 8:
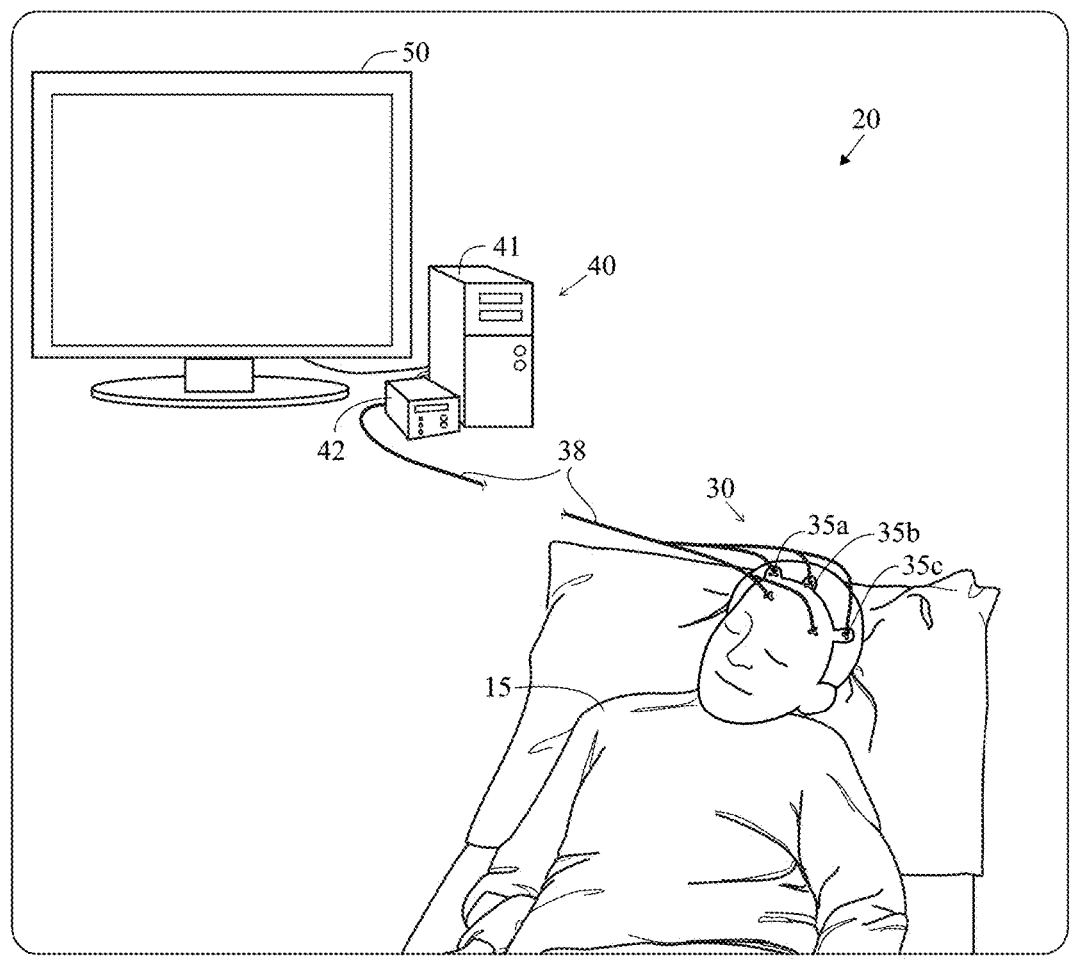
FIG. 8 is an illustration of an EEG system used on a patient.
Figure 11:
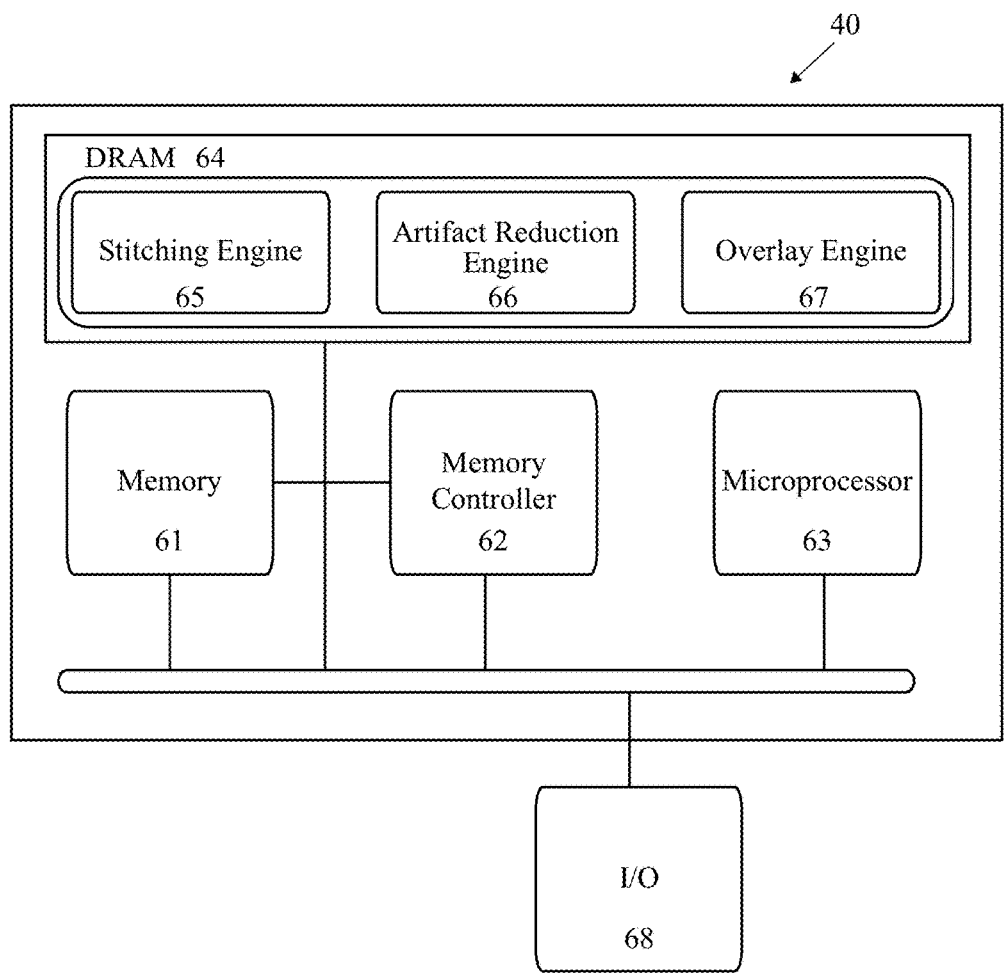
FIG. 11 is a block diagram of an EEG machine component of an EEG system.

As shown in FIG. 8, an EEG system is generally designated 20. The system preferably includes a patient component 30, an EEG machine component 40 and a display component 50. The patient component 30 includes a plurality of electrodes 35a, 35b, 35c attached to the patient 15 and wired by cables 38 to the EEG machine component 40. The EEG machine component 40 comprises a CPU 41 and an amplifier component 42. The EEG machine component 40 is connected to the display component 50 for display of the combined EEG reports, and for switching from a processed EEG report to the combined EEG reports, or from the processed EEG report to an original EEG report. As shown in FIG. 11, the EEG machine component 40 preferably includes a stitching engine 65, an artifact reduction engine 66, an overlay engine 67, a memory 61, a memory controller 62, a microprocessor 63, a DRAM 64, and an Input/Output 68. Those skilled in the pertinent art will recognize that the machine component 40 may include other components without departing from the scope and spirit of the present invention.

Figure 9:
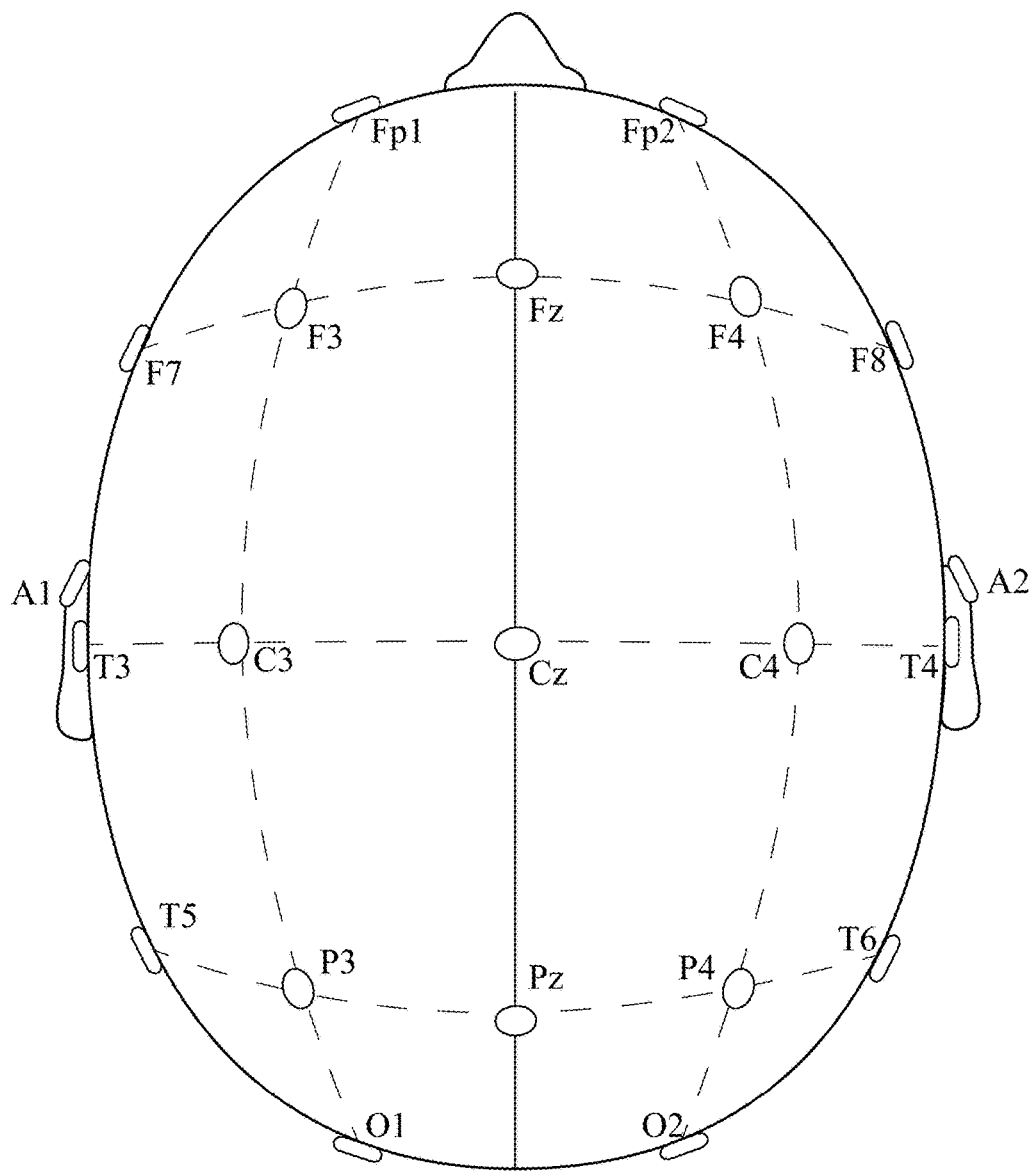
FIG. 9 is a map representing the international 10-20 electrode system for electrode placement for an EEG.
Figure 10:
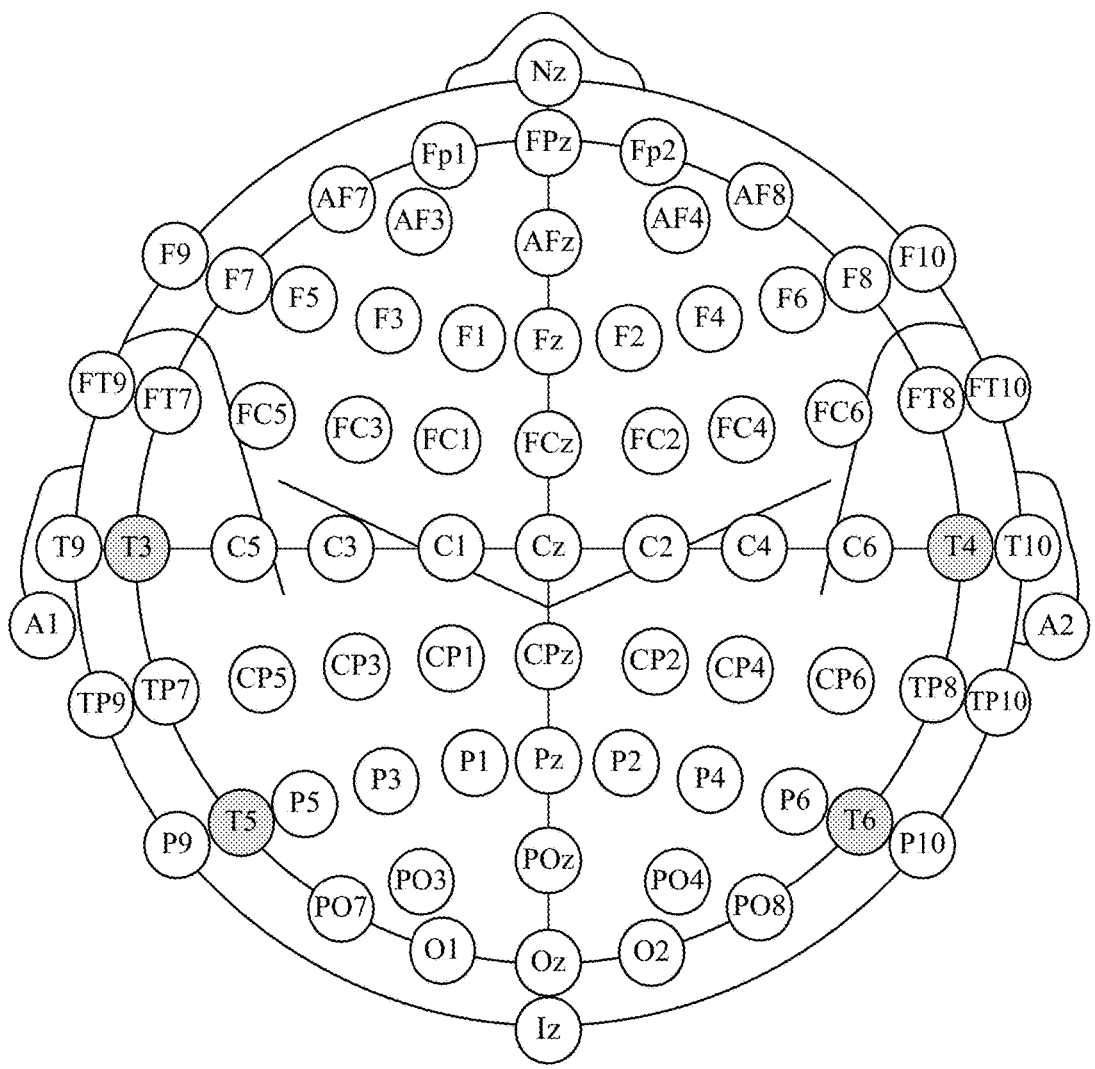
FIG. 10 is a detailed map representing the intermediate 10% electrode positions, as standardized by the American Electroencephalographic Society, for electrode placement for an EEG.

A patient has a plurality of electrodes attached to the patient's head with wires from the electrodes connected to an amplifier for amplifying the signal to a processor, which is used to analyze the signals from the electrodes and create an EEG recording. The brain produces different signals at different points on a patient's head. Multiple electrodes are positioned on a patient's head as shown in FIGS. 9 and 10. For example, Fp1 on FIG. 9 is represented in channel FP1-Ref on FIG. 5. The number of electrodes determines the number of channels for an EEG. A greater number of channels produce a more detailed representation of a patient's brain activity. Preferably, each amplifier 42 of an EEG machine component 40 corresponds to two electrodes 35 attached to a patient's 15 head. The output from an EEG machine component 40 is the difference in electrical activity detected by the two electrodes. The placement of each electrode is critical for an EEG report since the closer the electrode pairs are to each other, the less difference in the brainwaves that are recorded by the EEG machine component 40. A more thorough description of an electrode utilized with the present invention is detailed in Wilson et al., U.S. Pat. No. 8,112,141 for a Method And Device For Quick Press On EEG Electrode, which is hereby incorporated by reference in its entirety. The EEG is optimized for automated artifact filtering. The EEG recordings are then processed using neural network algorithms to generate a processed EEG recording, which is analyzed for display.

Algorithms for removing artifact from EEG typically use Blind Source Separation (BSS) algorithms like CCA (canonical correlation analysis) and ICA (Independent Component Analysis) to transform the signals from a set of channels into a set of component waves or "sources." The sources that are judged as containing artifact are removed and the rest of the sources are reassembled into the channel set.

Figure 12:
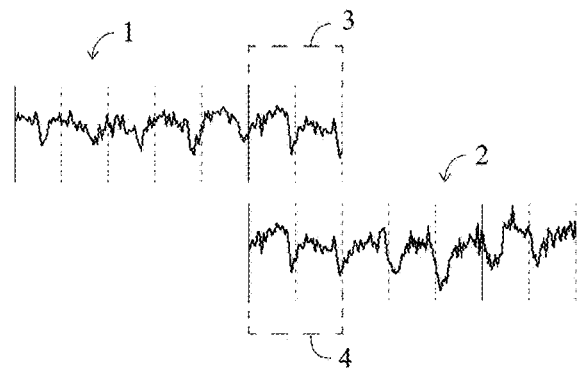
FIG. 12 is an illustration of isolated adjacent epochs.

FIG. 12 is an isolated view of adjacent unprocessed epochs 1 and 2. Epoch 1 has an overlapping portion 3 and epoch 2 has an overlapping portion 4. In this example, the overlapping portions 3 and 4 are approximately two seconds in length. Thus, overlapping portions 3 and 4 represent the same timeframe (two seconds) for raw EEG recording.

Figure 13:
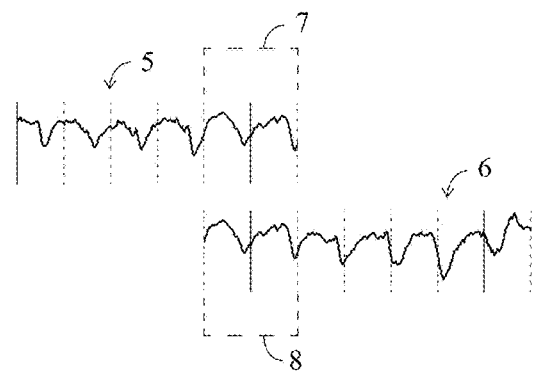
FIG. 13 is an illustration of isolated adjacent epochs.

FIG. 13 is an illustration of adjacent processed epochs 5 and 6. Artifact reduction has been performed on these epochs 5 and 6. Processed epochs 5 and 6 represent the same timeframe as unprocessed epochs 1 and 2. Thus, epoch 5 is the result of artifact reduction of unprocessed epoch 1, and epoch 6 is the result of artifact reduction of unprocessed epoch 2. Processed epoch 5 has an overlapping portion 7 and processed epoch 6 has an overlapping portion 8. Thus, overlapping portions 7 and 8 represent the same timeframe (two seconds) for the processed EEG recording. Further, overlapping portion 7 is the same timeframe as overlapping portion 3 and overlapping portion 8 is the same timeframe as overlapping portion 4. Further overlapping portions 3, 4, 7 and 8 represent all the same timeframe.

Figure 14:
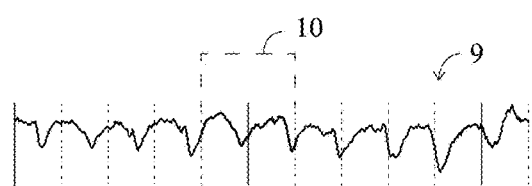
FIG. 14 is an illustration of epochs stitched together with an overlapping portion.

FIG. 14 is an illustration of the stitching of adjacent processed epochs 5 and 6 into a section of continuous processed EEG recording 9. Portion 10 is the overlapping portions 7 and 8 from adjacent processed epochs 5 and 6. As shown, no information is lost, and the processed EEG recording is continuous, without abrupt termination points where epochs have been stitched together.

Figure 15:
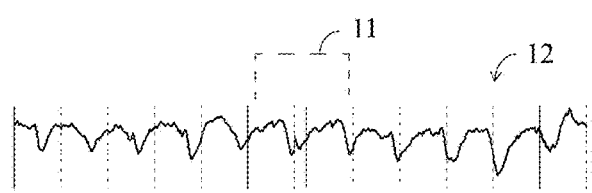
FIG. 15 is an example of prior art combining of epochs resulting in discontinuous or missing information from the processed and stitched EEG recording.

FIG. 15 is an illustration of the prior art approach of stitching of epochs without overlapping portions. The section 12 of the processed EEG recording has a stitching portion 11, which has changed from the same timeframe of the processed epochs 5 and 6. The stitching portion 11 is different from section 10 of FIG. 14.

Figure 16:
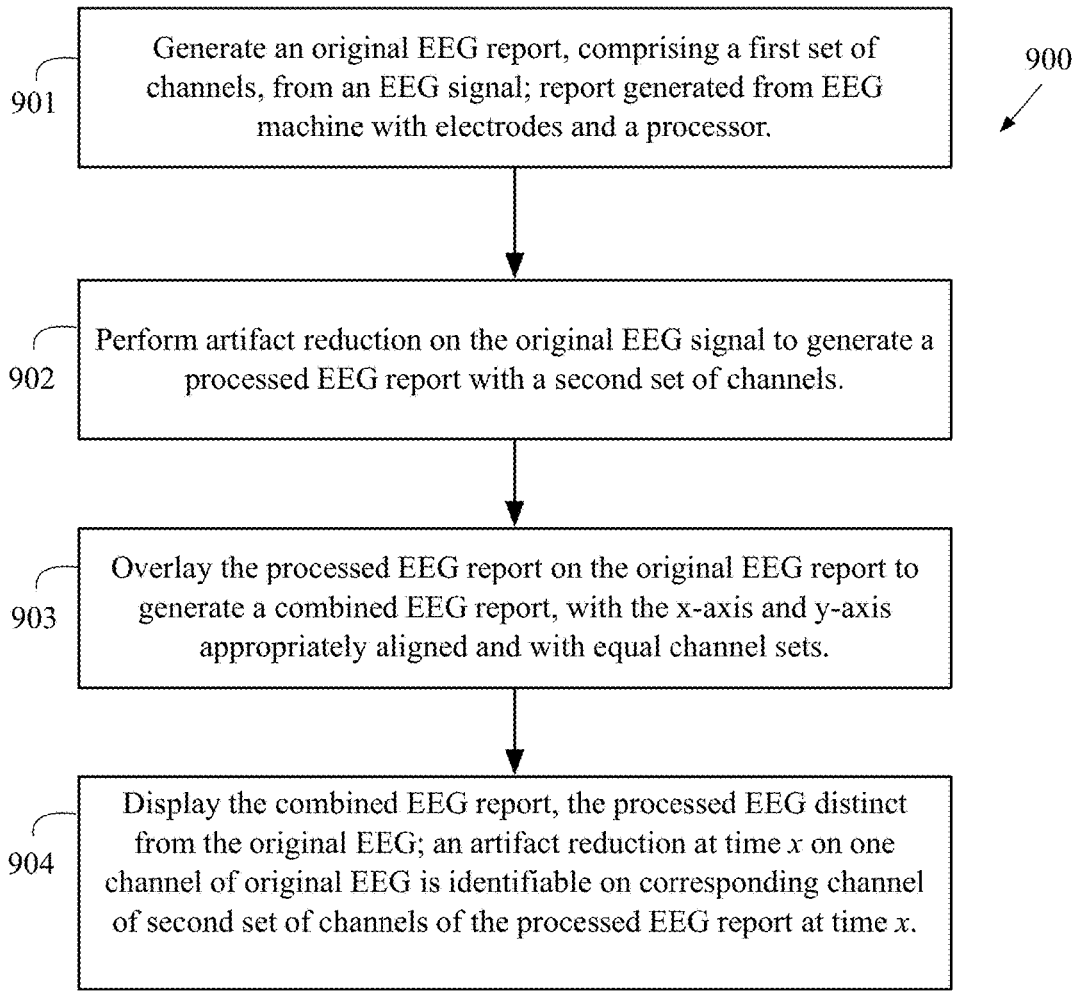
FIG. 16 is a flow chart of a method for displaying EEG data.
Figure 17:
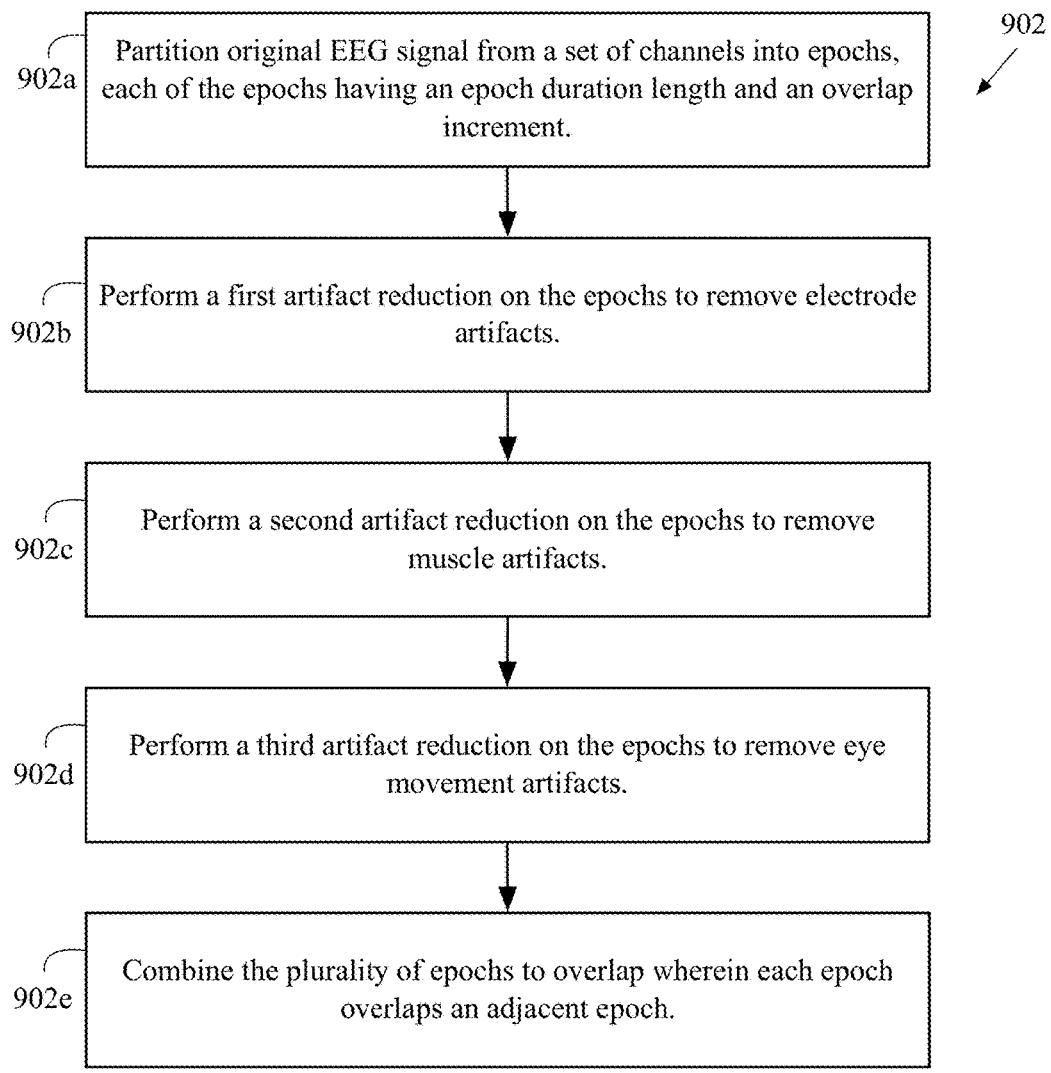
FIG. 17 is a flow chart for a method of artifact reduction.

A flow chart for a method 900 for displaying EEG data is shown in FIG. 16. At block 901, an original EEG report is generated from an EEG signal. The original EEG report is generated from an EEG machine comprising a plurality of electrodes and processor. The original EEG report comprises a first plurality of channels. At block 902, artifact reduction is performed on the original EEG signal to generate a processed EEG report. The processed EEG report comprises a second plurality of channels. At block 903, the processed EEG report overlays the original EEG report to generate a combined EEG report. An x-axis of the processed EEG report is aligned with an x-axis of the original EEG report. A y-axis of the processed EEG report is aligned with a y-axis of the original EEG report. The first plurality of channels of the original EEG report are equal to the second plurality of channels of the processed EEG report. At block 904, the combined EEG report is displayed on a display screen, preferably a monitor. The processed EEG report is visually distinctive from the original EEG report. An activity at a specific time on one channel of the first plurality of channels of the original EEG report is identifiable on a corresponding channel of the second plurality of channels of the processed EEG report at the specific time. The activity is preferably spikes, sharp waves, spike and wave discharges, artifacts, and the like FIG. 17 is a flow chart of a preferred method 902 for artifact reduction of raw EEG data. At block 902*a*, the original EEG signal is portioned from a set of channels into a plurality of epochs. Each of the plurality of epochs having an epoch duration length and an overlap increment. At block 902*b*, a first artifact reduction is performed on the plurality of epochs to remove electrode artifacts. At block 902*c*, a second artifact reduction is performed on the plurality of epochs to remove muscle artifacts. At block 502*d*, a third artifact reduction is performed on the plurality of epochs to remove eye movement artifacts. At block 902*e*, the plurality of epochs is combined to overlap wherein each epoch of the plurality of epochs overlaps an adjacent epoch to form a processed continuous EEG report.

Each of the plurality of epochs has an epoch duration length of two seconds and an increment of one second. Alternatively, each of the plurality of epochs has an epoch duration length of four seconds and an increment of two seconds. The artifact removal algorithm is preferably a blind source separation algorithm. The blind source separation algorithm is preferably a CCA algorithm or an ICA algorithm. The clean epochs are preferably combined using a weighted average and the weight of the weighted average is preferably proportional to the ratio of the distance to an epoch center.

Figure 18:
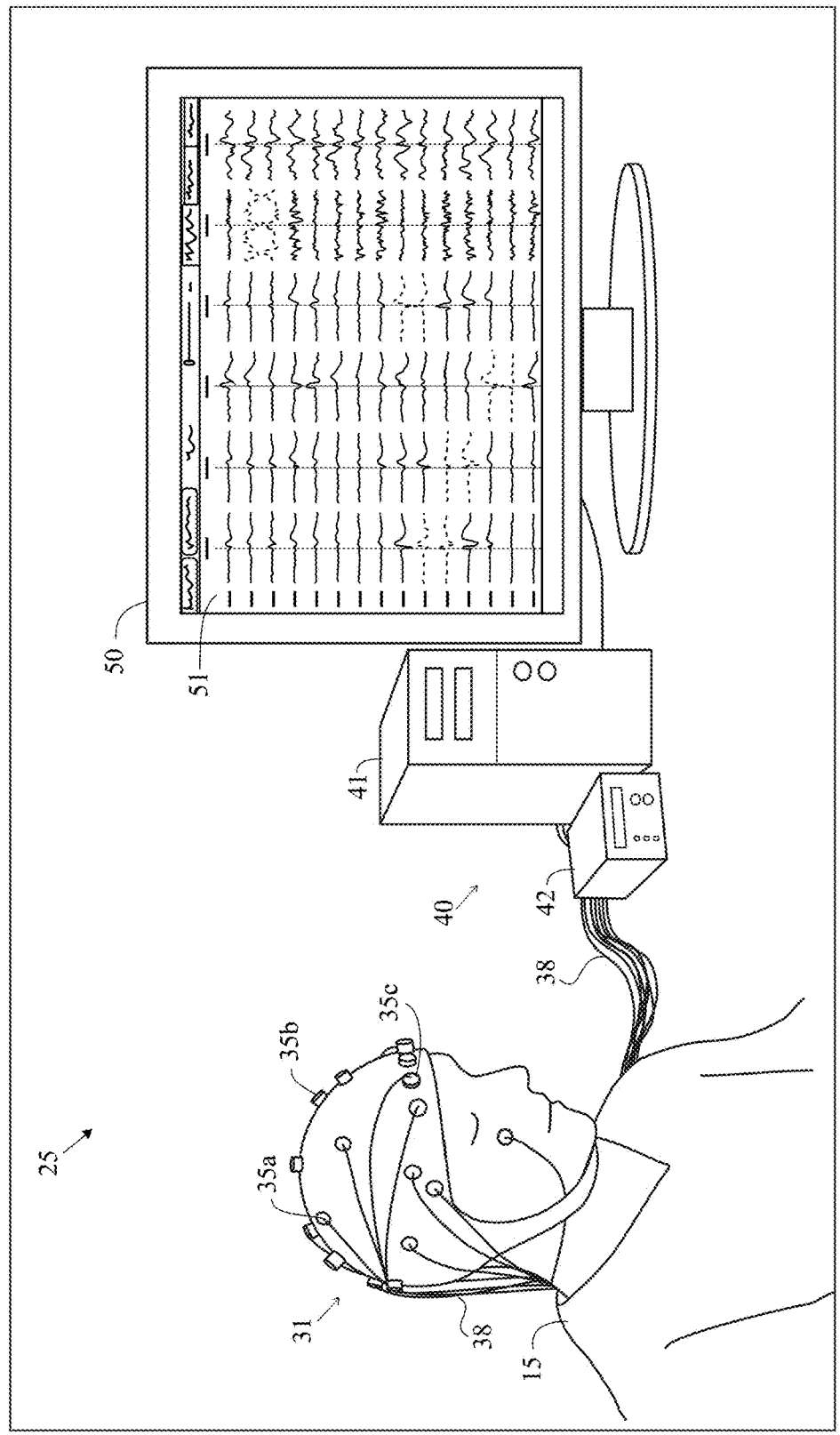
FIG. 18 is a block diagram of a system for analyzing an EEG recording.

FIG. 18 illustrates a system 25 for a user interface for automated artifact filtering for an EEG. A patient 15 wears an electrode cap 31, consisting of a plurality of electrodes 35*a*-35*c*, attached to the patient's head with wires 38 from the electrodes 35 connected to an EEG machine component 40 which consists of an amplifier 42 for amplifying the signal to a computer 41 with a processor, which is used to analyze the signals from the electrodes 35 and create an EEG recording 51, which can be viewed on a display 50. A button on computer 41, either through a keyboard or touchscreen button on display 50 allows for the application of a plurality of filters to remove the plurality of artifacts from the EEG and generate a clean EEG. A more thorough description of an electrode utilized with the present invention is detailed in Wilson et al., U.S. Pat. No. 8,112,141 for a Method And Device For Quick Press On EEG Electrode, which is hereby incorporated by reference in its entirety. The EEG is optimized for automated artifact filtering. The EEG recordings are then processed using neural network algorithms to generate a processed EEG recording which is analyzed for display.

FIGS. 19-23 illustrate analyzed EEG recordings. An additional description of analyzing EEG recordings is set forth in Wilson et al., U.S. patent application Ser. No. 13/620855, filed on Sep. 15, 2012, for a Method And System For Analyzing An EEG Recording, which is hereby incorporated by reference in its entirety.

Figure 19:
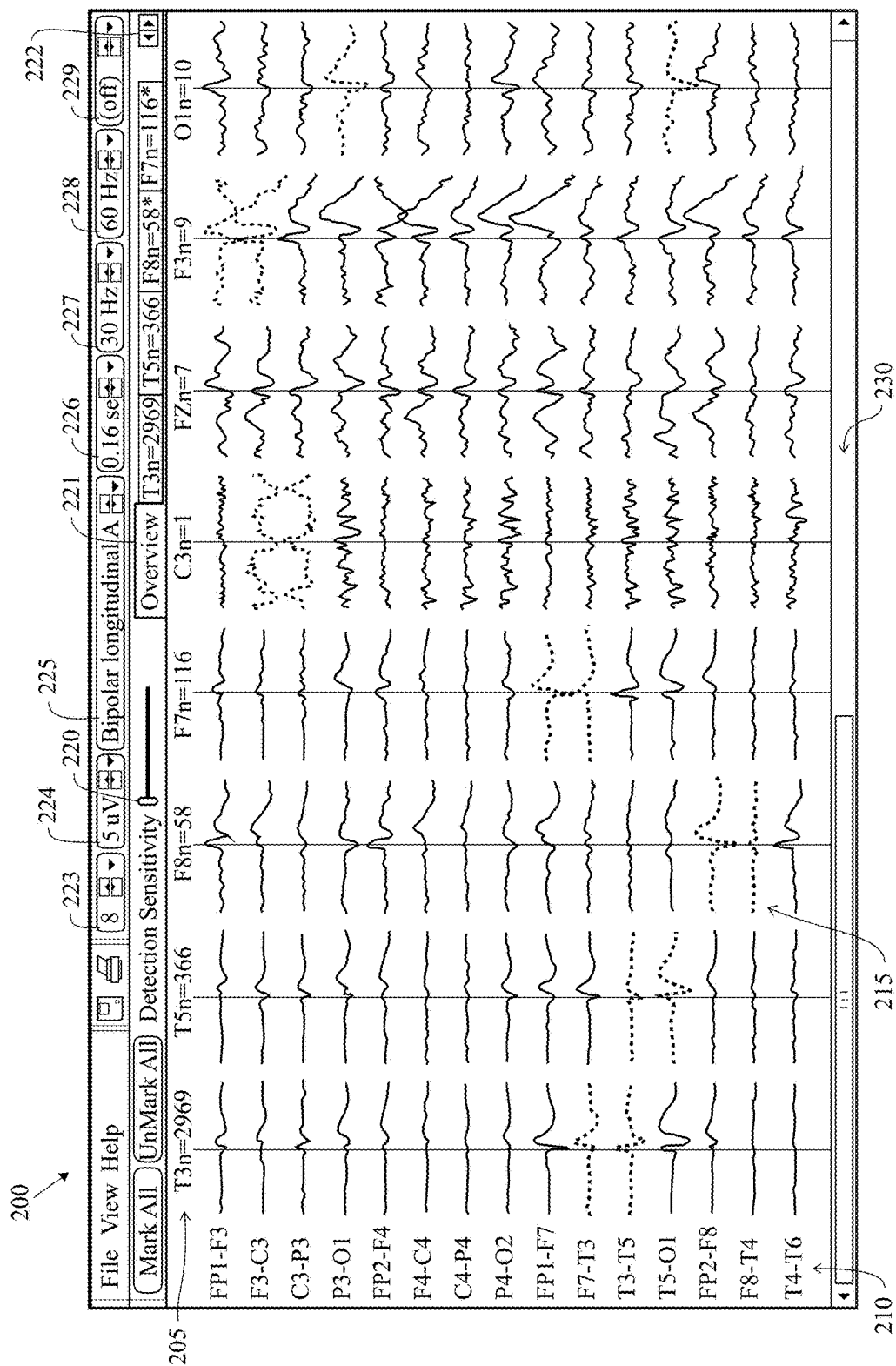
FIG. 19 is an illustration of an analyzed EEG recording.
Figure 20:
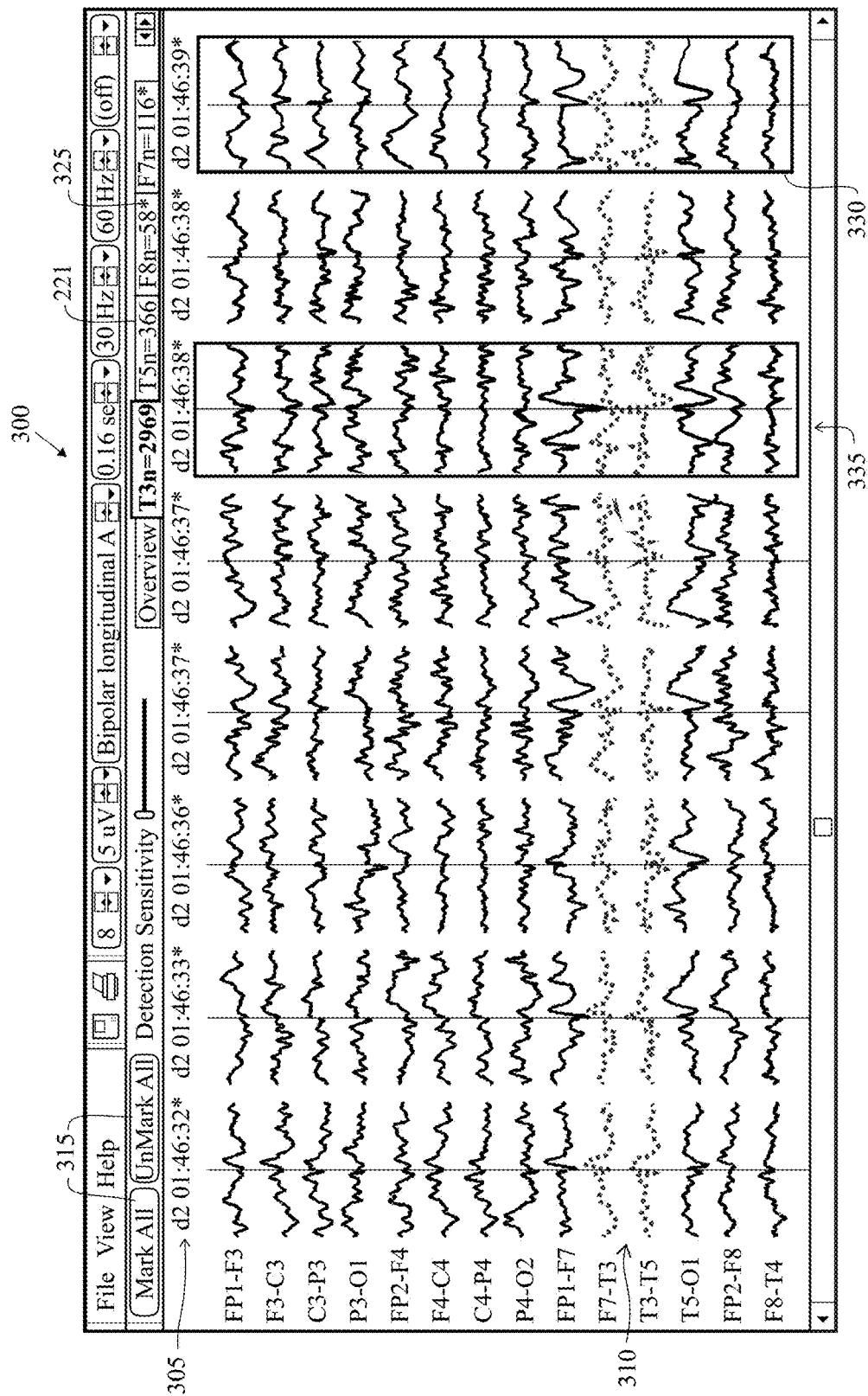
FIG. 20 is an illustration of an analyzed EEG recording.

When the Easy SpikeReview program opens, the Overview window 200 is initially presented, as shown in FIG. 19. The overview depicts averages from the various spike foci detected by a spike detection mechanism. To create these overview averages the spike detections are sorted by detection foci (electrode) and then all detections at a particular focus are mathematically averaged. For example, the first column of EEG represents an average of 2969 events that had their maximum point of detection at the T3 electrode. The columns of the EEG are preferably separated from other columns by a thin band of white. Each EEG column represents a distinct group average. The primary electrode focal point of each average, and the number of detection events incorporated into each average, 205 are shown above the columns of EEG. Channels including the detection focal point electrode are highlighted red 215. As with evoked potentials, averaging multiple detections results in an increase in the signal-to-noise ratio and makes it easier to delineate the field of distribution of epileptiform abnormalities.

The various functions of the Easy SpikeReview window include the ability to choose spike detections per page 223, an EEG voltage amplitude selector 224, a montage selector 225, LFF (TC) 226, HFF 227, notch 228, and a custom filter 229. Navigation to other tabs not in the current view is also possible with the forward and back tabs 222. If there's more than one page of Overview averages, clicking on the bottom bar 230 will page forward. Right-clicking on the montage bar 210 will show montage controls.

The sensitivity of the SpikeDetector output can be dynamically adjusted during the review process, which is done by using the detection sensitivity slider 220 that is labeled. When Easy SpikeReview is initially opened, the detection sensitivity slider 220 is set to the far left position. In this position the SpikeDetector neural network algorithms identify sharp transients that have a high probability of being epileptiform abnormalities: these are events the detector assigned a high probability of being a real epileptiform abnormality. The rate of false positive detections at this setting is lowest. Thus, the ratio of true epileptiform signal to false positive noise is highest at this setting. However, some spikes and sharp waves that are less well-formed may not be evident with the slider set at its lowest sensitivity. The detector's sensitivity can be quickly adjusted by dragging the slider 220 towards the right so that it is more sensitive and thus more likely to identify less well-formed or lower amplitude transients. New groups may then appear in the overview display of spike averages. In concert with the increase in true spike detections, there is also an increase in false positive detections.

In records with rare epileptiform abnormalities or those in which the SpikeDetector neural networks, when set to lowest sensitivity, do not recognize the epileptiform abnormalities well, switching to the highest setting on the detection sensitivity slider 220 may allow visualization of real epileptiform abnormalities. In such cases, identifying the rare events often requires assessment of the individual raw detections. This is accomplished by either displaying all raw detections back-to-back following the spike averages on the overview page, or by reviewing the detections at each electrode location, such as in FIG. 20, by progressively selecting the location tabs 221 at the top of the EEG window. Detections that have already been viewed are marked with a trailing asterisk 325 behind the time.

Figure 21:
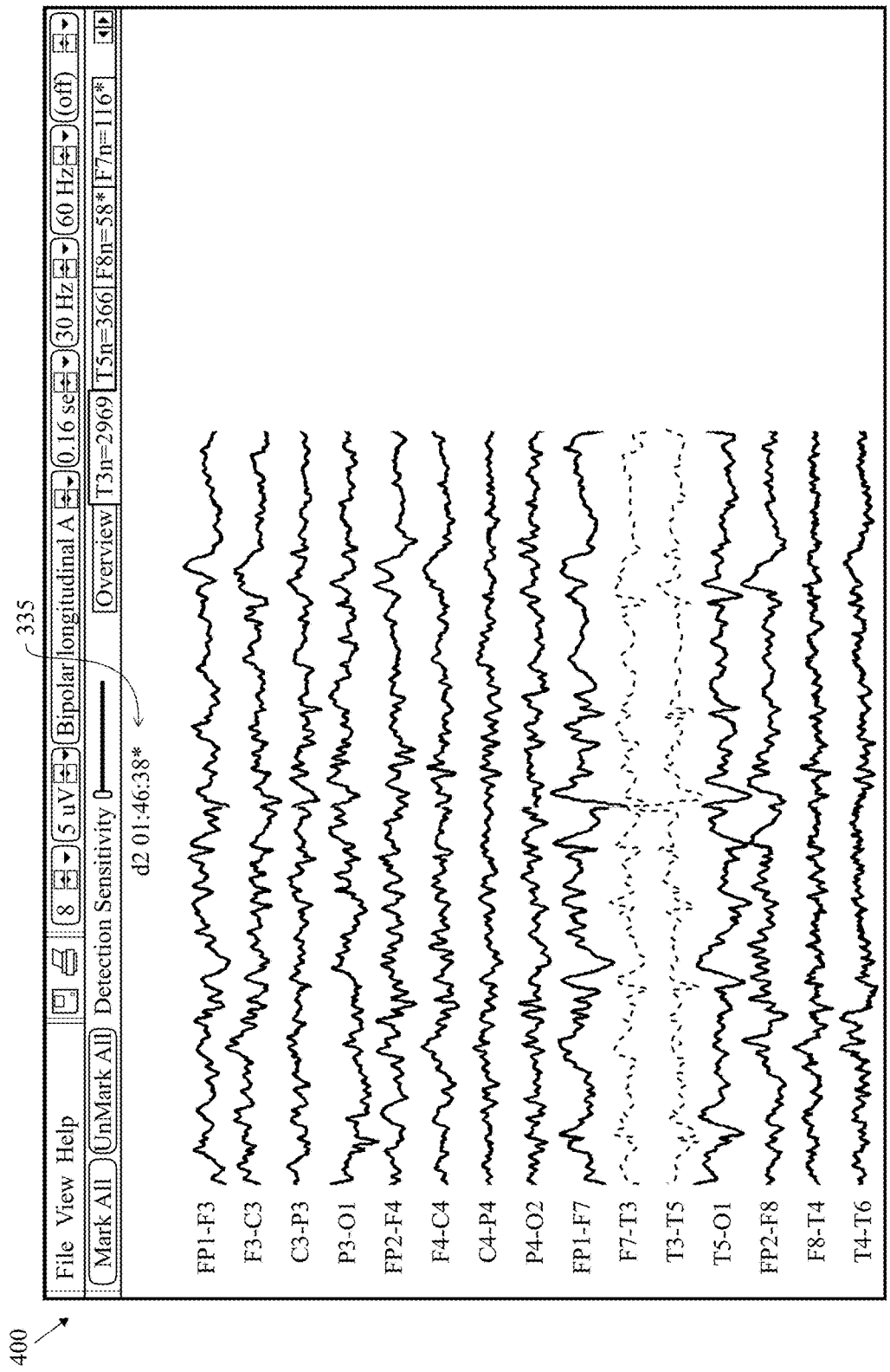
FIG. 21 is an illustration of an analyzed EEG recording.

Clicking on any of the electrode location tabs 221 at the top of the EEG window will display the raw (non-averaged) spike detections 300 that arose from that particular electrode location. The individual detections are separated by a thin band of white, and the detection point is centered in a one second segment of EEG and indicated by a faint vertical gray line with a heading indicating the time of detection 305. Channels containing the electrode involved in the detection are highlighted red 310. Left double-clicking with the mouse on any individual detection 335 will cause an expanded EEG view 400, as shown in FIG. 21, of that particular detection 335 to appear. Left double-clicking on the expanded view 400 will return the user to a display of back-to-back individual detections 300.

Figure 22:
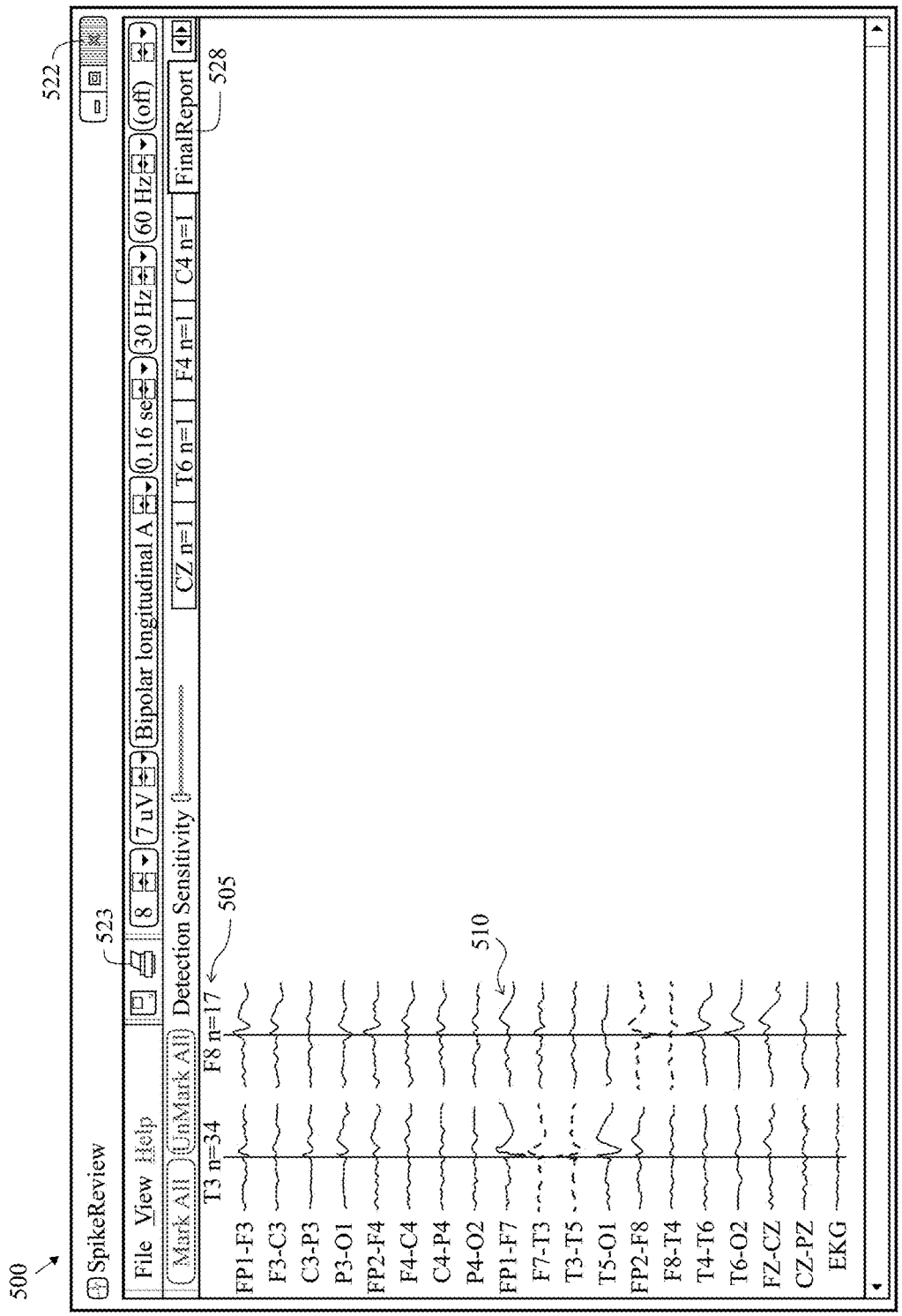
FIG. 22 is an illustration of an analyzed EEG recording.

When viewing individual spike detections (accessed from the tabs 221 above the EEG window), exemplar spikes can be hand-marked by left-clicking with the mouse on the desired example. A rectangle outlining the chosen spike 330 will appear. Marking all or unmarking all detections can be done with the Mark All or UnMark All buttons 315 on the toolbar. Hand-marked detections will be included in the spike averages that appear in the FinalReport. These hand-marked events can also be displayed back-to-back, as shown in FIG. 22, immediately following their averages in FinalReport 500, and can be printed 523 for archival purposes or for evaluation by another reviewer.

Figure 23:
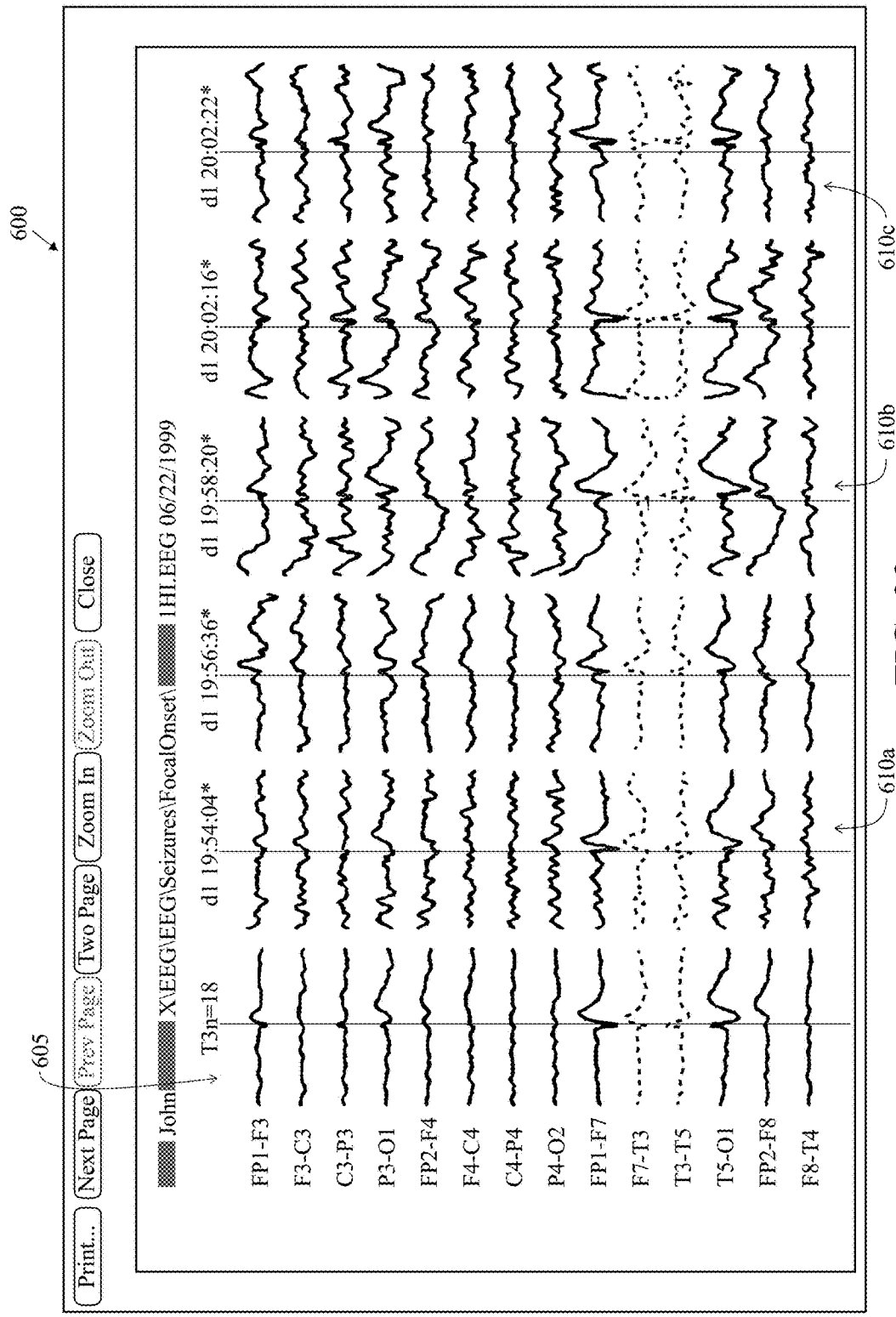
FIG. 23 is an illustration of an analyzed EEG recording.

Clicking on FinalReport tab 528 at the top of the EEG window displays a summary of all hand-marked exemplar spike or sharp waves 510 at the focus 505 chosen. The initial default view shows the mathematical averages of the user-chosen hand-marked events, sorted by electrode focus 505. As explained, head voltage topograms and back-to-back individual user-selected events are displayed by selecting menu options or via right mouse click choices. Voltage topograms are only created when viewing the EEG in a referential montage. FIG. 23 is a print preview view 600 of a FinalReport showing a group average of 18 user-selected spikes 605 and constituent spikes 610a-610c. Upon exiting 522 the program, all changes are automatically saved, including user marked spikes and viewed events.

Figure 24:
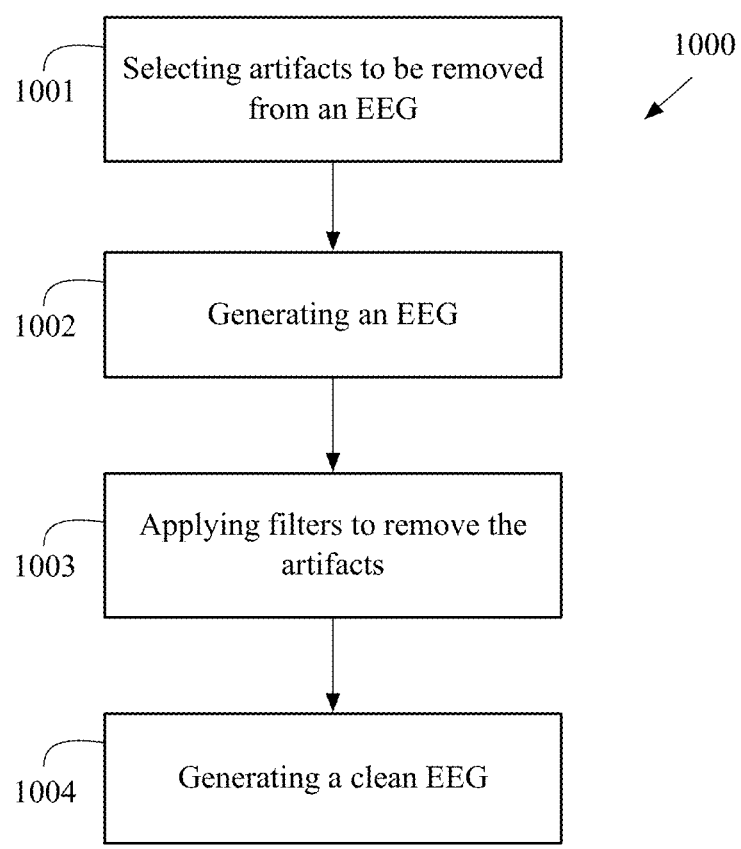
FIG. 24 is a flow chart of a general method.

FIG. 24 is a flow chart of a general method 1000 for removing artifacts from an EEG recording. At block 1001, a plurality of artifacts is selected to be automatically removed from an EEG recording using a user interface. At block 1002 an EEG is generated. At block 1003, a plurality of filters is applied to remove the plurality of artifacts from the EEG. At block 1004, a clean EEG is generated.

Figure 25:
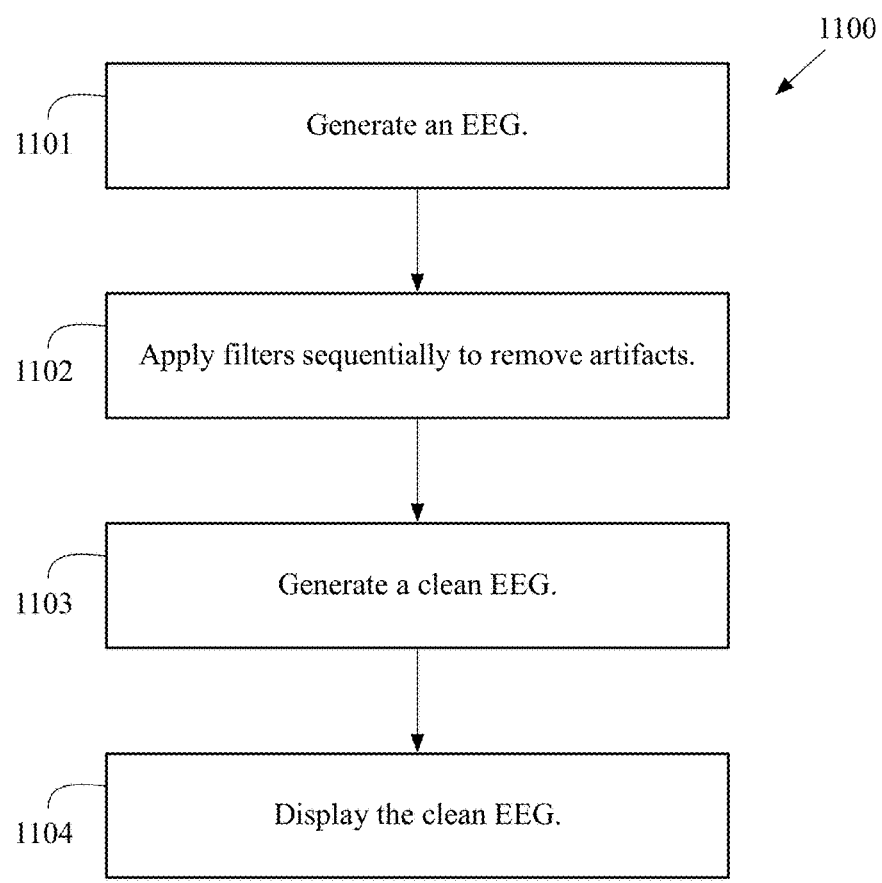
FIG. 25 is a flow chart of a specific method.

FIG. 25 is a flow chart of another method 1100 for removing artifacts from an EEG recording. At block 1101, an EEG is generated from a machine comprising a plurality of electrodes, an amplifier and processor. At block 1102, multiple filters are applied sequentially to remove artifacts from the EEG. At block 1103, a clean EEG is generated. At block 1104, the clean EEG is displayed.

Figure 26:
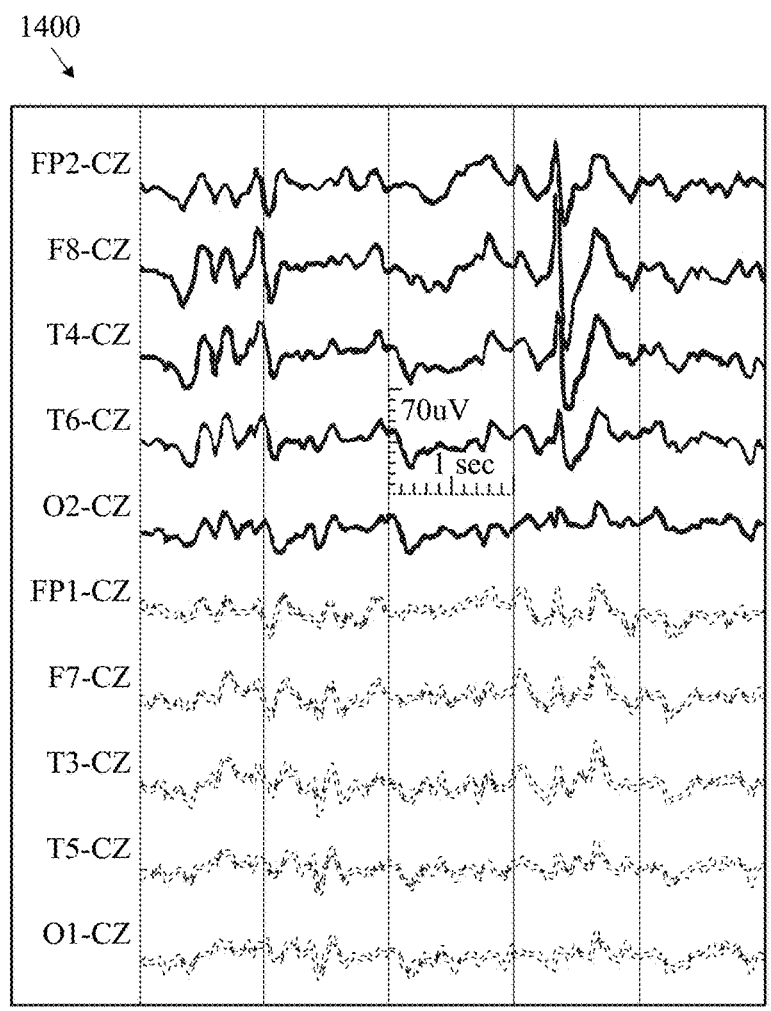
FIG. 26 is an illustration of a CZ reference montage.

FIG. 26 is an illustration of a CZ reference montage 1400.

In one example an algorithm called BSS-CCA is used to remove the effects of muscle activity from the EEG. Using the algorithm on the recorded montage will frequently not produce optimal results. In this case it is generally optimal to use a montage where the reference electrode is one of the vertex electrodes such as CZ in the international 10-20 standard. In this algorithm the recorded montage would first be transformed into a CZ reference montage prior to artifact removal. In the event that the signal at CZ indicates that it is not the best choice then the algorithm would go down a list of possible reference electrodes in order to find one that is suitable.

It is possible to perform BSS-CCA directly on the user-selected montage. However this has two issues. First this requires doing an expensive artifact removal process on each montage selected for viewing by the user. Second the artifact removal will vary from one montage to another, and will only be optimal when a user selects a referential montage using the optimal reference. Since a montage that is required for reviewing an EEG is frequently not the same as the one that is optimal for removing artifact this is not a good solution.

The artifact removal algorithm is preferably a blind source separation algorithm. The blind source separation algorithm is preferably a CCA algorithm or an ICA algorithm.

Figure 27:
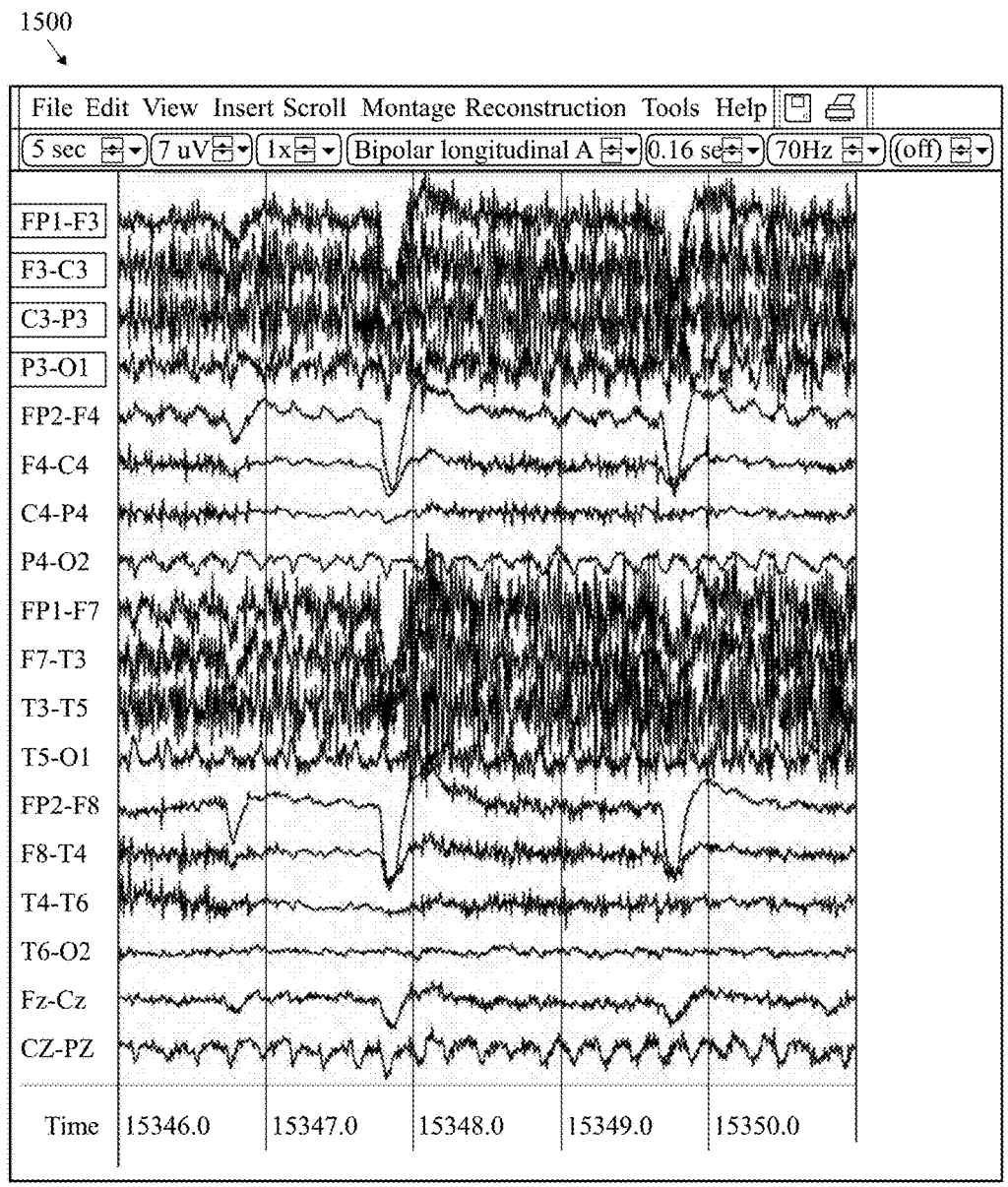
FIG. 27 is an illustration of an EEG recording containing a seizure, a muscle artifact and an eye movement artifact.
Figure 28:
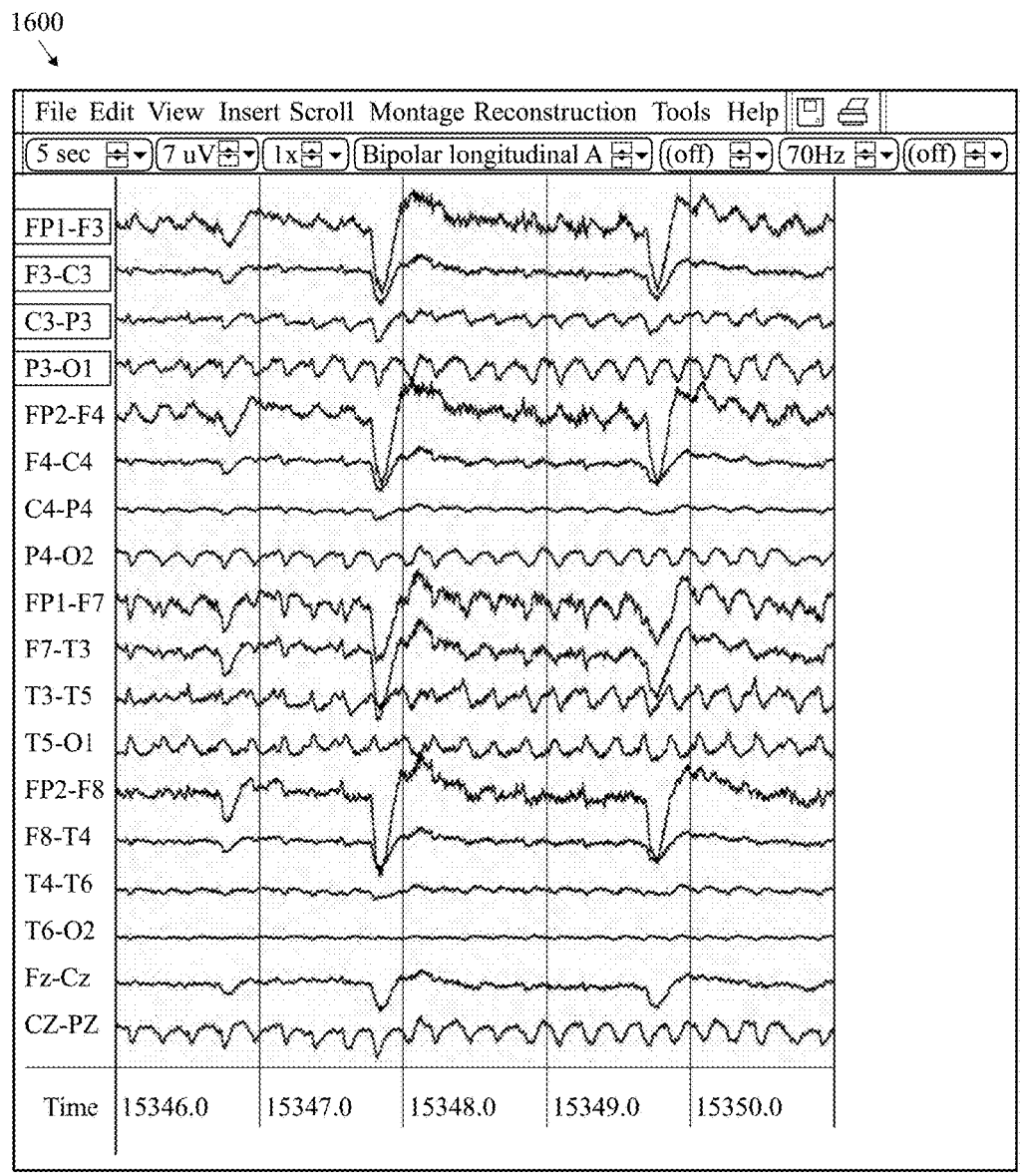
FIG. 28 is an illustration of the EEG recording of FIG. 15 with the muscle artifact removed.
Figure 29:
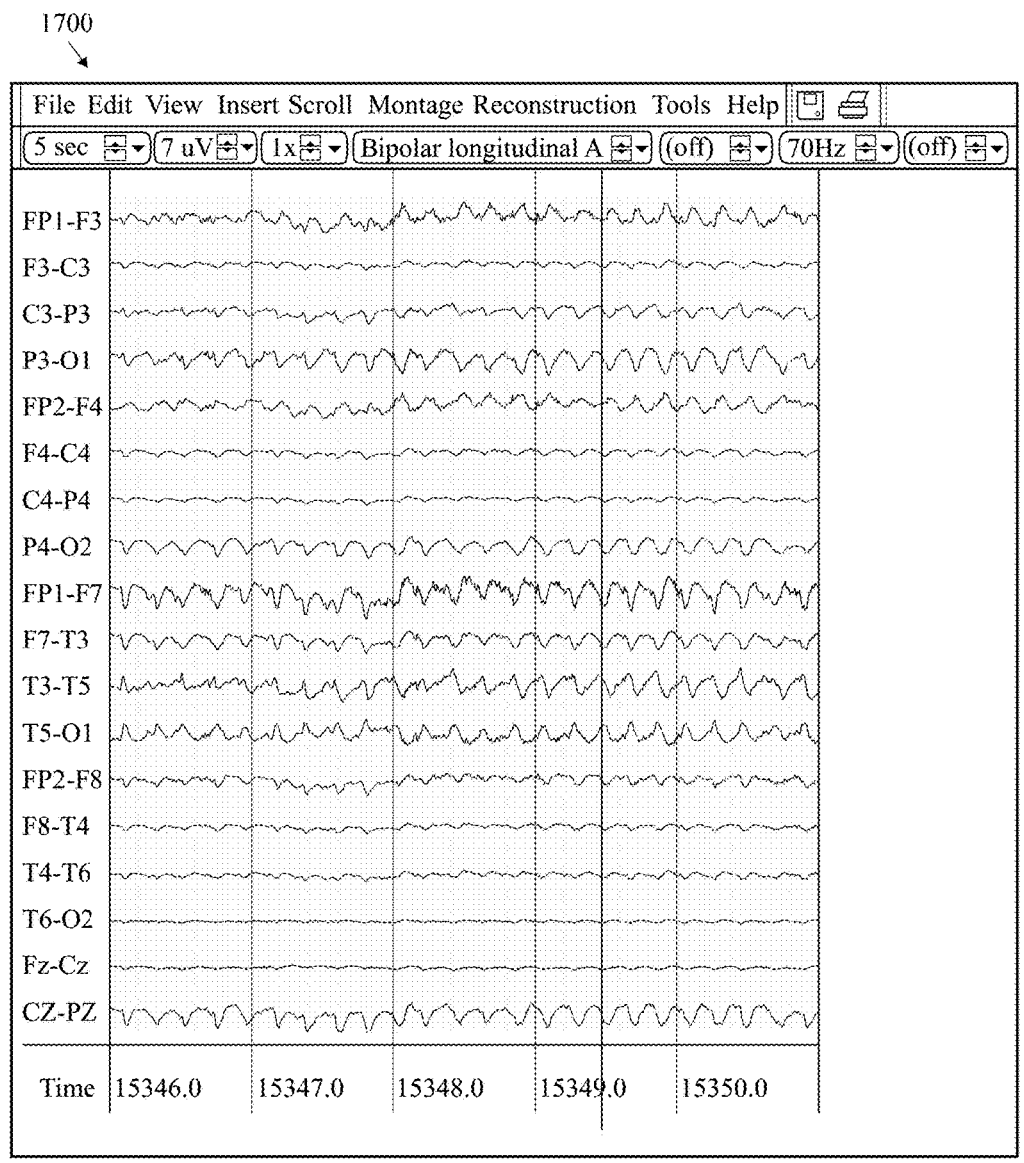
FIG. 29 is an illustration of the EEG recording of FIG. 16 with the eye movement artifact removed.

FIGS. 27-29 illustrate how removing artifacts from the EEG signal allow for a clearer illustration of a brain's true activity for the reader. FIG. 27 is an illustration of an EEG recording containing a seizure, a muscle artifact and an eye movement artifact 1500. FIG. 28 is an illustration of the EEG recording of FIG. 27 with the muscle artifact removed 1600. FIG. 29 is an illustration of the EEG recording of FIG. 28 with the eye movement artifact removed 1700.

Figure 30:
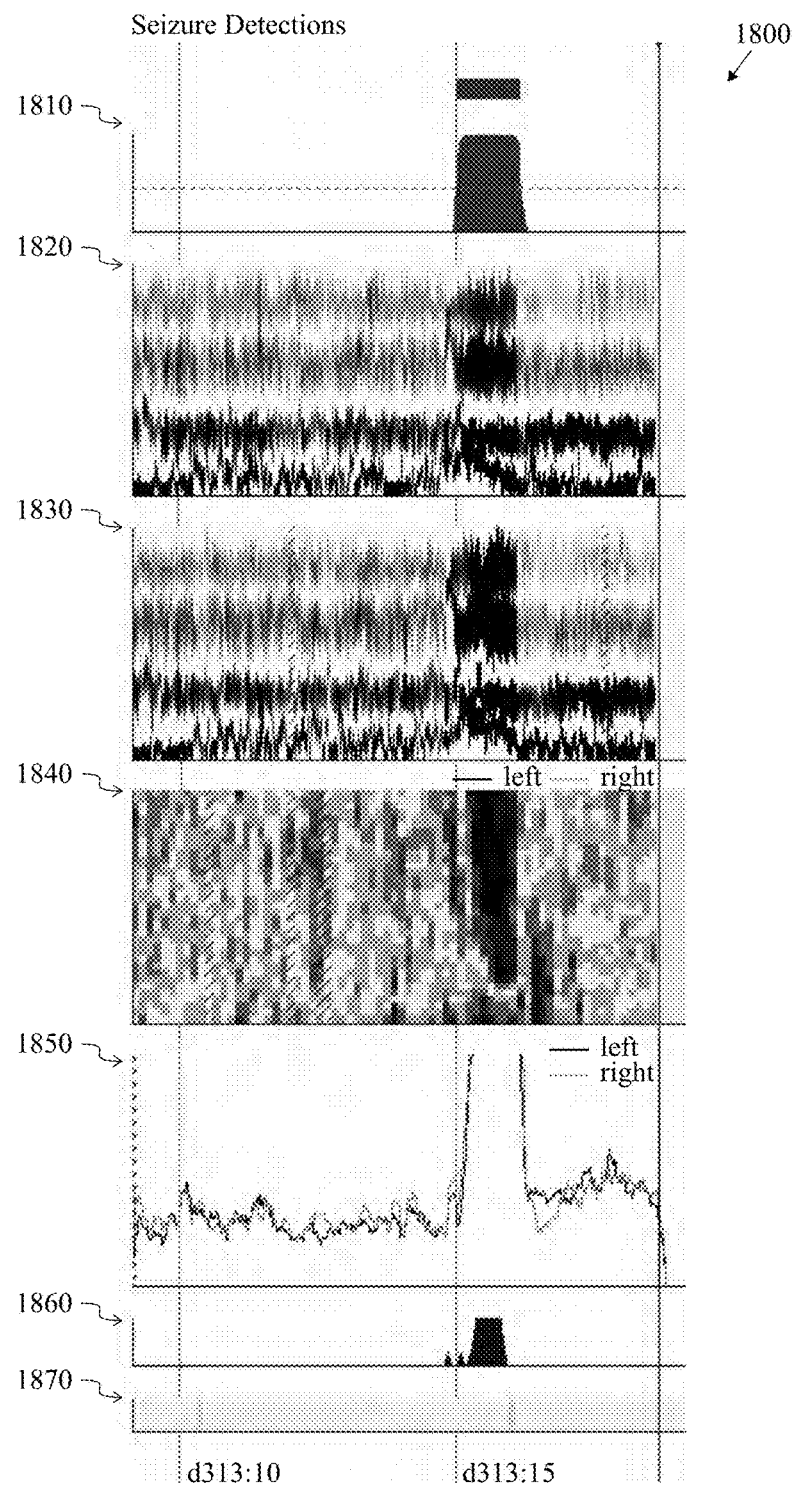
FIG. 30 is an illustration of spike detections indicative of a seizure.

FIG. 30 is an illustration of spike detections indicative of a seizure 1800. Seizure probability 1810; Rhythmicity Spectrogram, left hemisphere, 1-25 Hz 1820; Rhythmicity Spectrogram, right hemisphere, 1-25 Hz 1830; Relative Asymmetry Spectrogram, Hemispheric, 0-18 Hz 1840; Peak Envelope, hemispheric, 2-20 Hz 1850; Spike Detections (count per 5 second epoch) 1860; Chewing Artifact Probability 1870.

Figure 31:
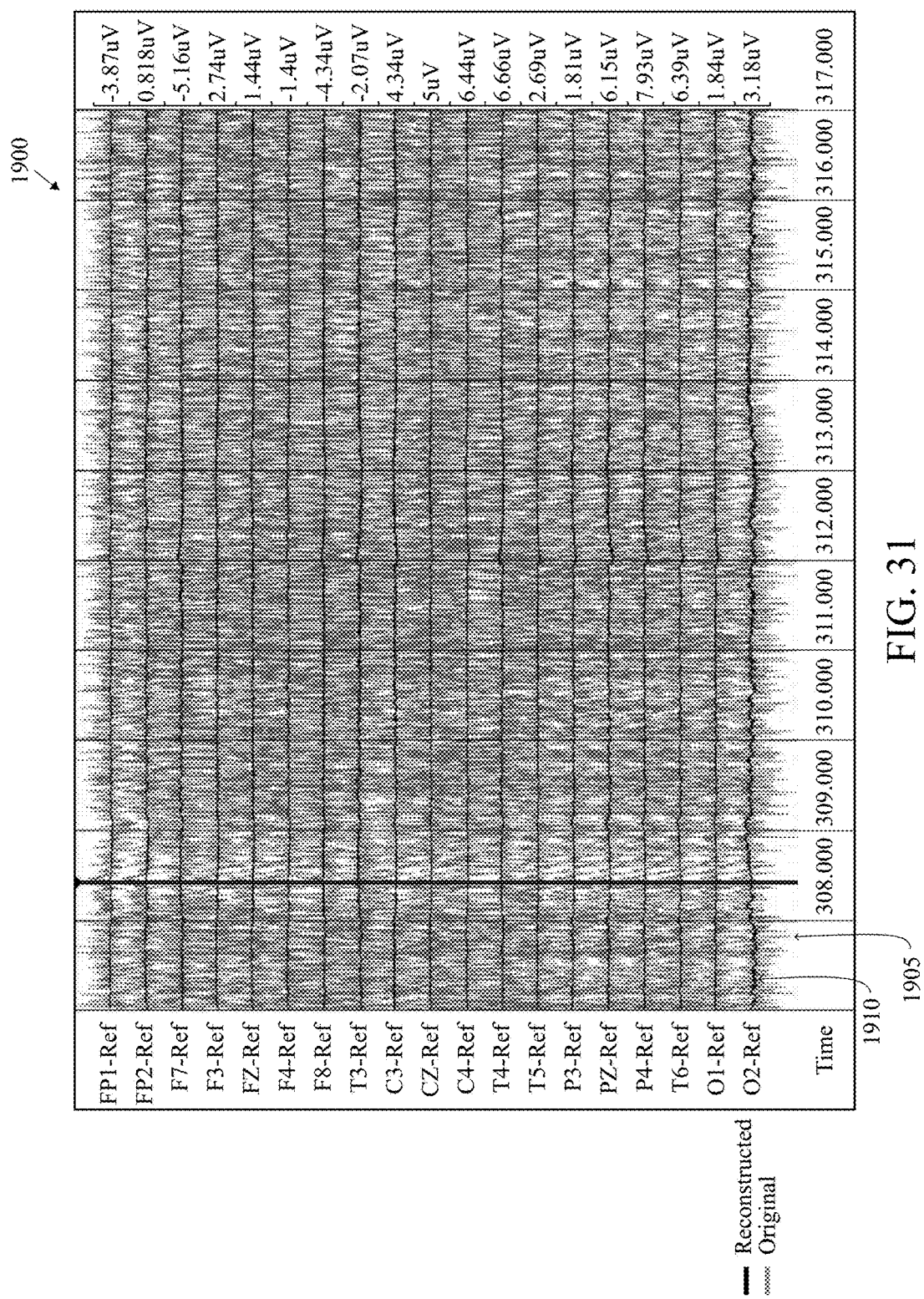
FIG. 31 is an illustration of a paralytic EEG record for a patient for a first time period of the EEG record after removing muscle artifacts using a recorded montage.
Figure 32:
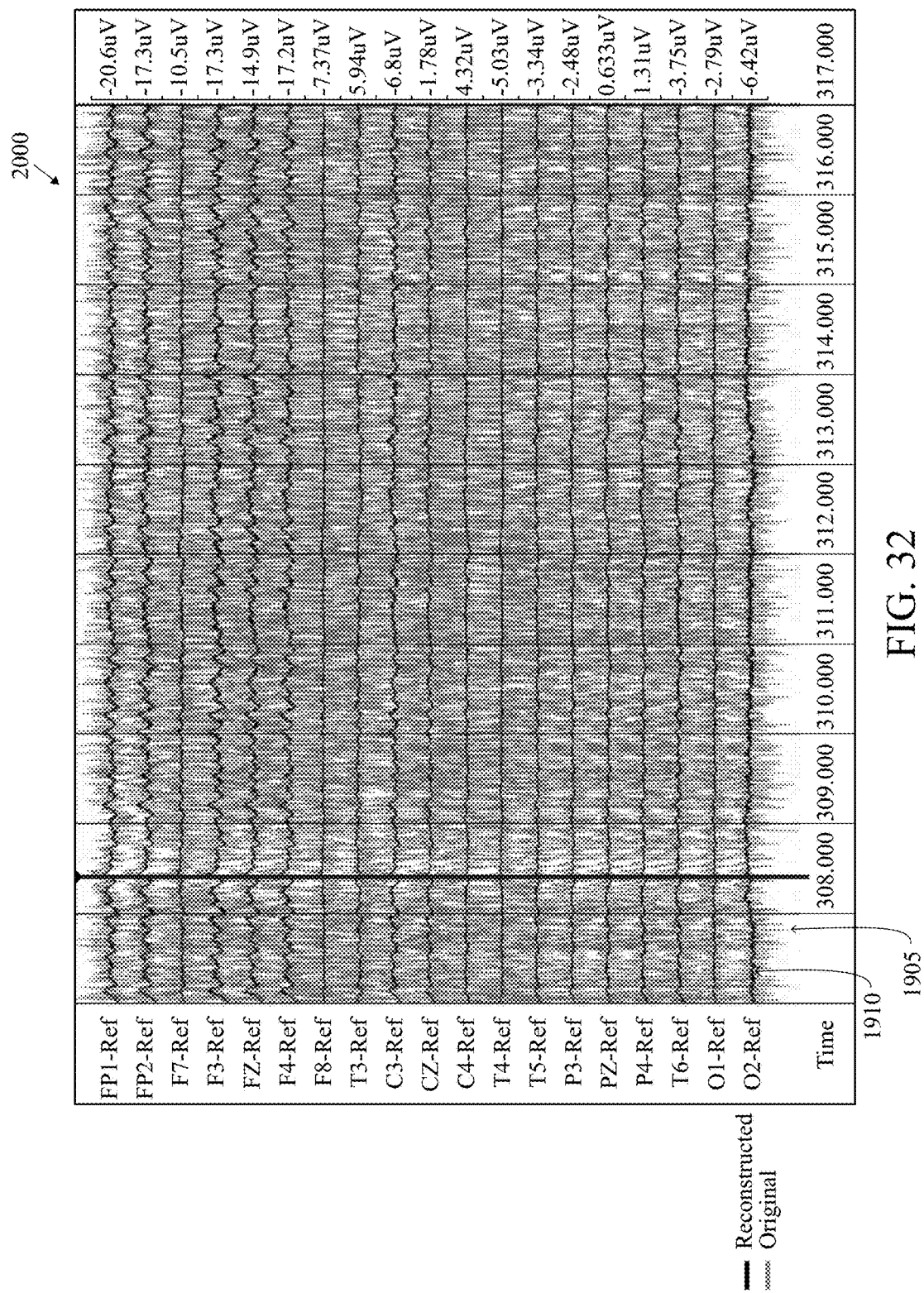
FIG. 32 is an illustration of a paralytic EEG record for a patient for a first time period of the EEG record after removing muscle artifacts using a CZ reference montage.
Figure 33:
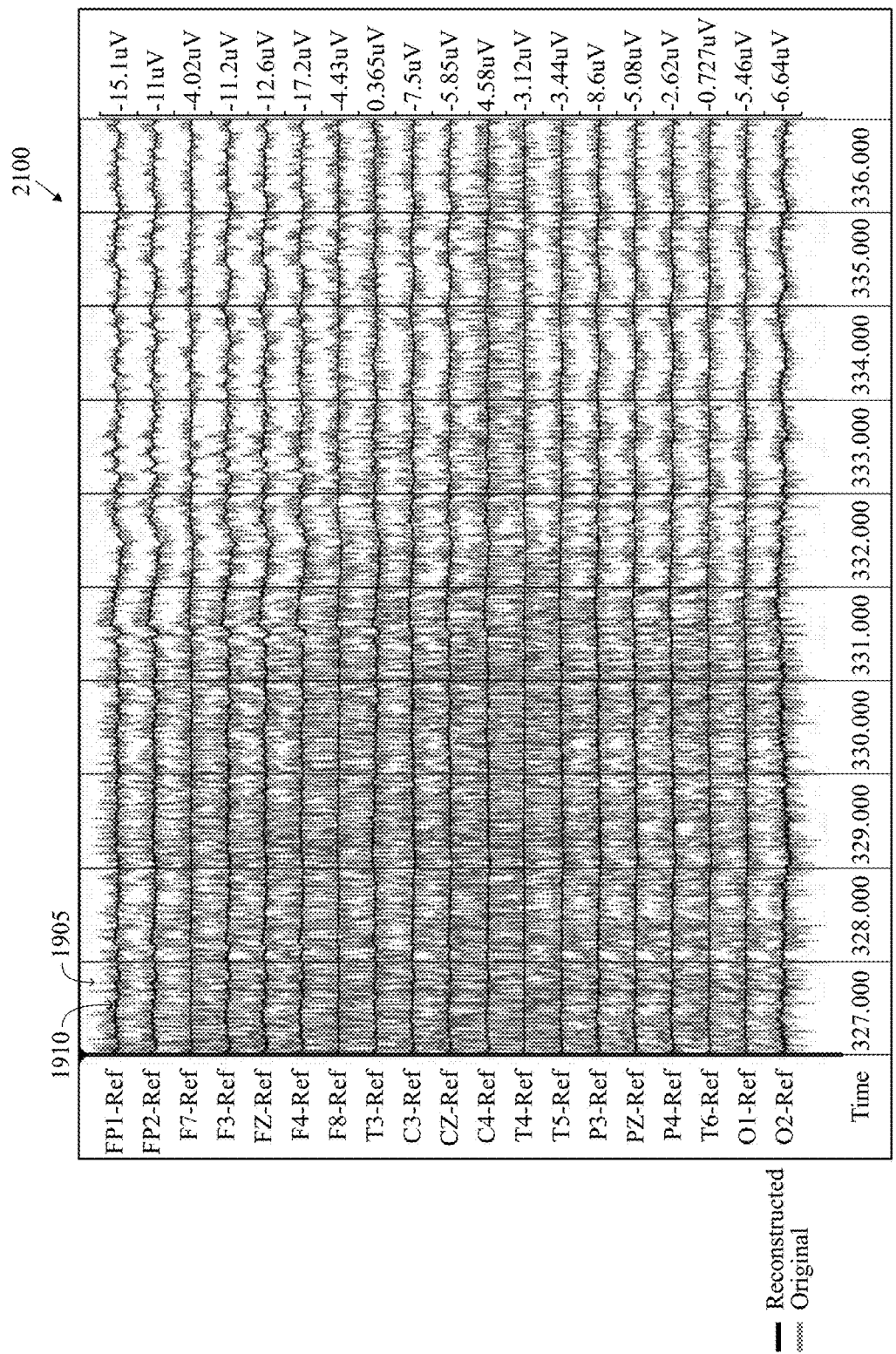
FIG. 33 is an illustration of a paralytic EEG record for a patient for a second time period of the EEG record after removing muscle artifacts using a recorded montage.
Figure 34:
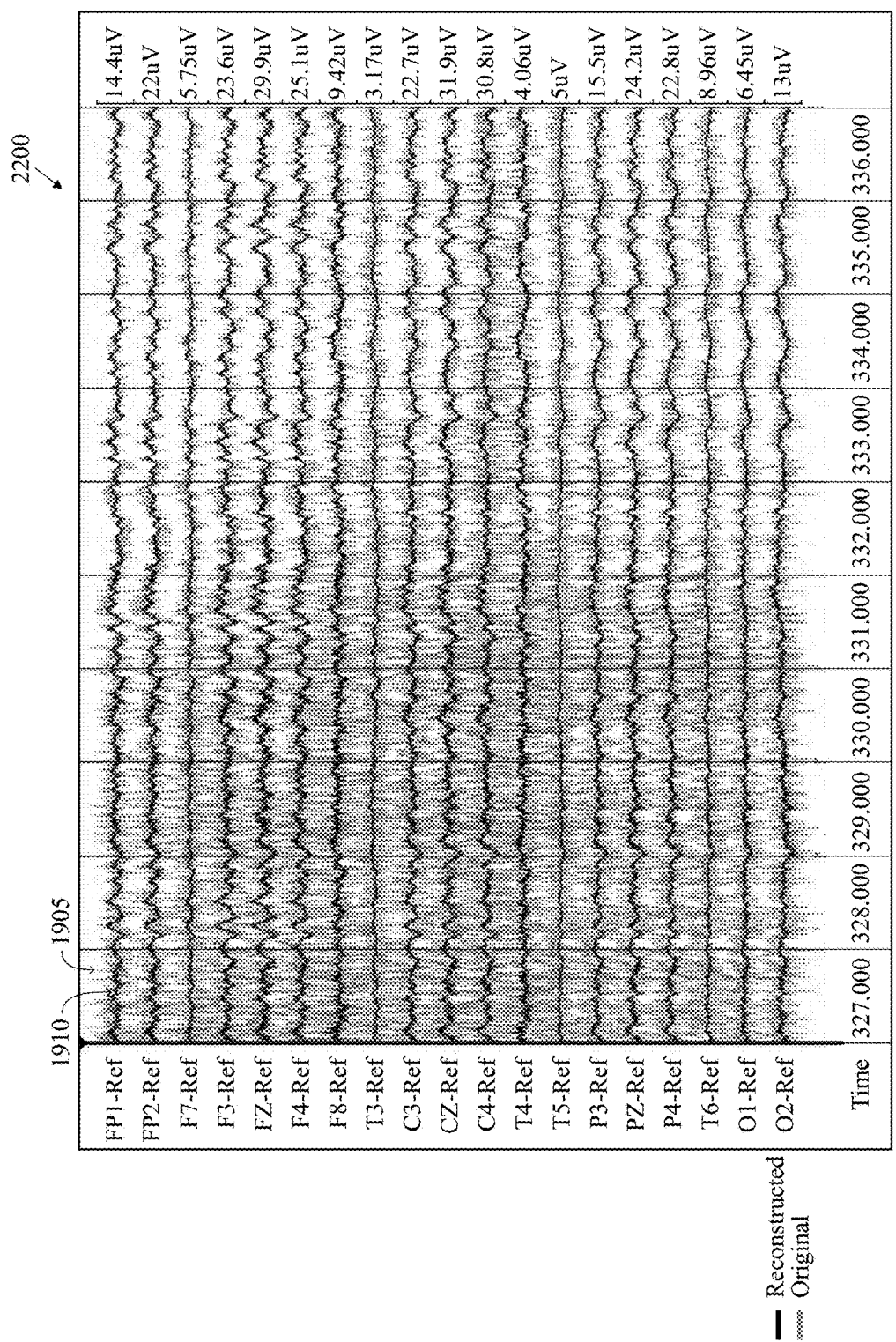
FIG. 34 is an illustration of a paralytic EEG record for a patient for a second time period of the EEG record after removing muscle artifacts using a CZ reference montage.
Figure 35:
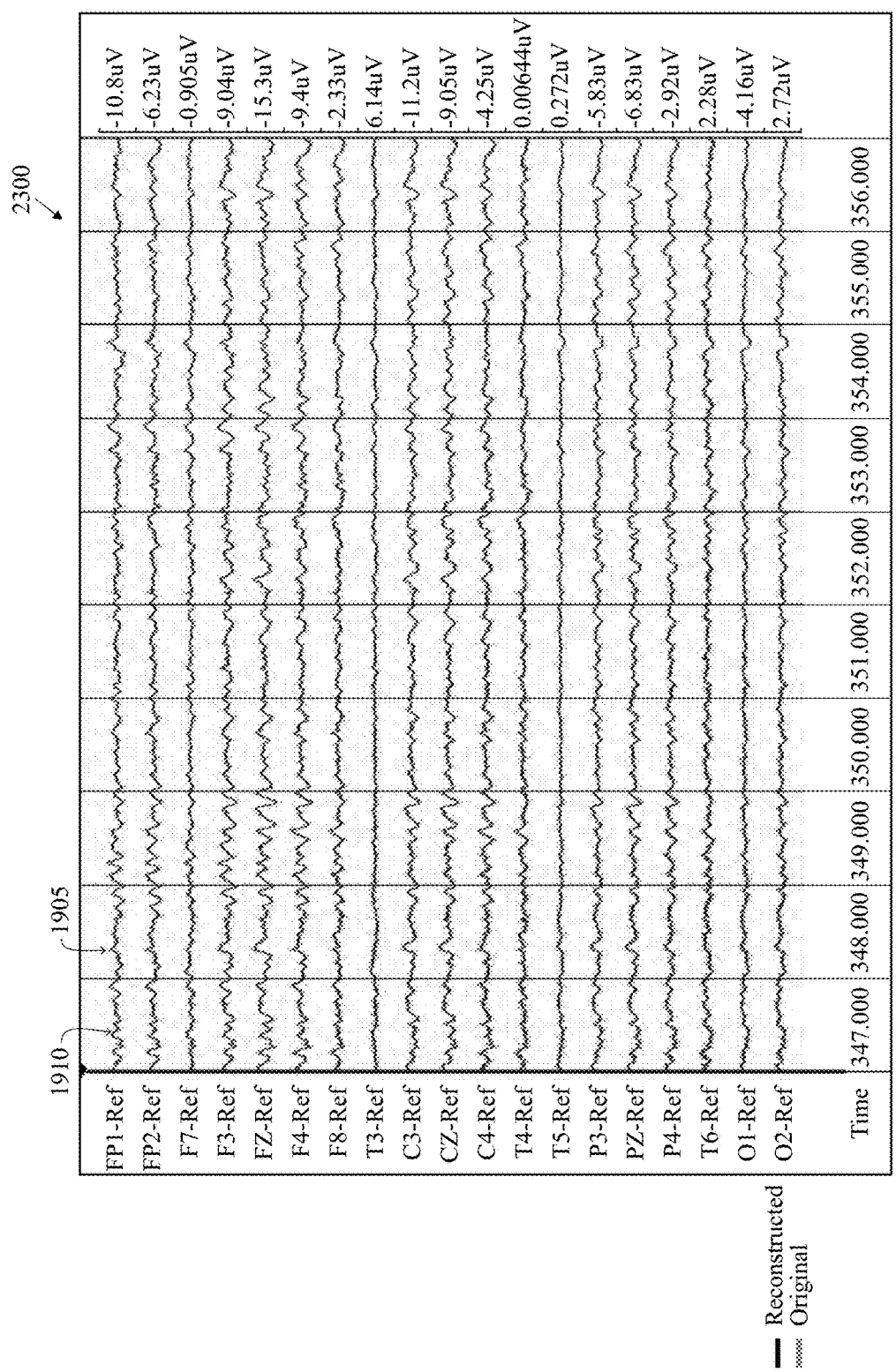
FIG. 35 is an illustration of a paralytic EEG record for a patient for a third time period (the patient has been paralyzed so the muscle activity is absent) of the EEG record after removing muscle artifacts using a recorded montage.
Figure 36:
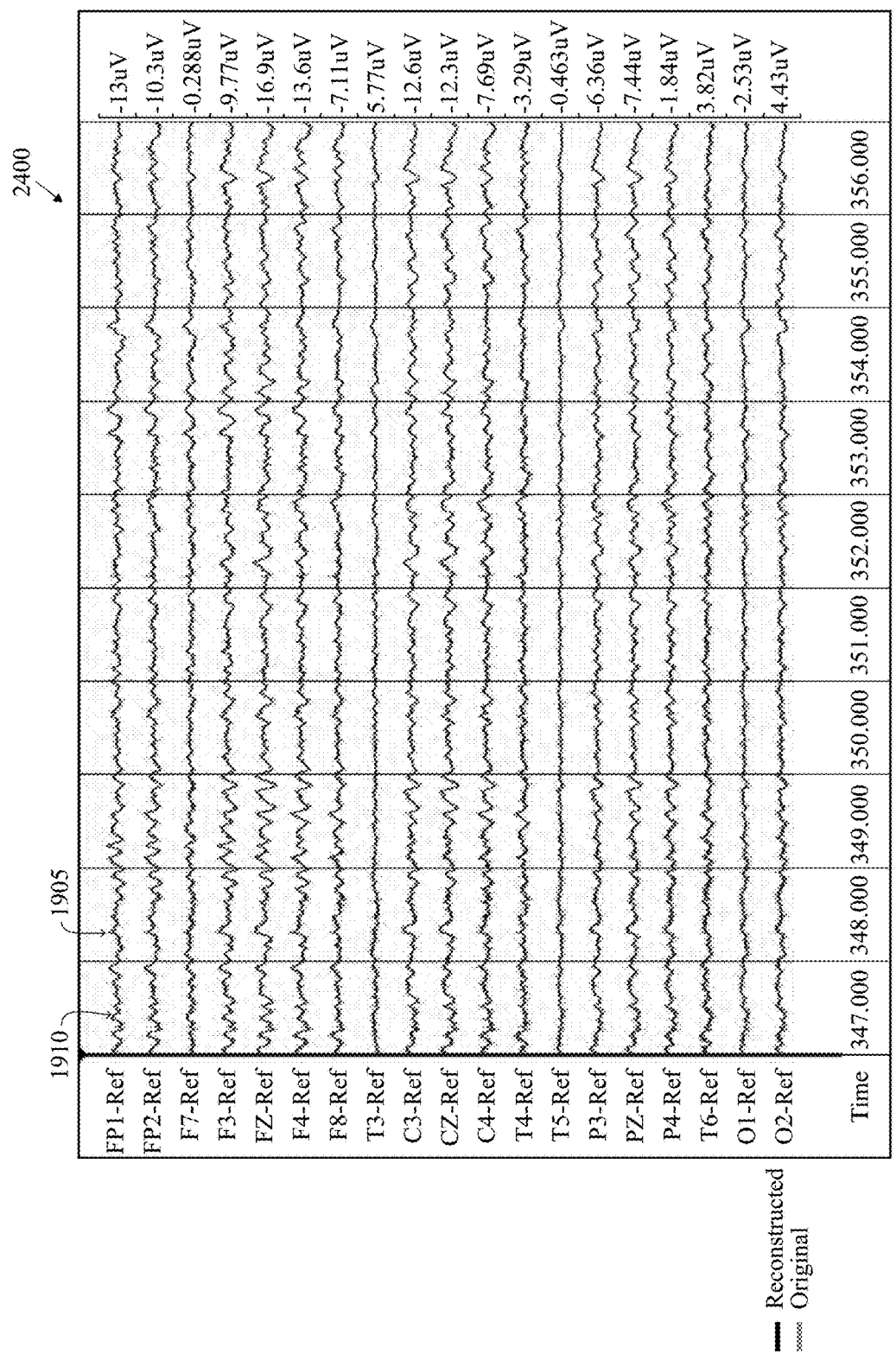
FIG. 36 is an illustration of a paralytic EEG record for a patient for a third time period (the patient has been paralyzed so the muscle activity is absent) of the EEG record after removing muscle artifacts using a CZ reference montage.

FIGS. 31, 33, and 35 are illustrations of a paralytic EEG record for a patient for three time periods (at the third time period the patient has been paralyzed so the muscle activity is absent 2300) of an EEG record after removing muscle artifacts using a recorded montage. FIGS. 32, 34, and 36 are illustrations of a paralytic EEG record for a patient for three time periods (at the third time period the patient has been paralyzed so the muscle activity is absent 2400) of an EEG record after removing muscle artifacts using a CZ reference montage. The red is the original signal 1905 and the black is the reconstruction 1910. Using the recorded montage, all of the brain activity is removed and the black reconstruction appears almost flat 1900, 2100, 2300. However, using the CZ reference montage, the brain activity is retained and appears in the first two time periods 2000, 2200 similar to the third time period 2400 when the patient is paralyzed.

Various artifact removal techniques are explained in U.S. Provisional Patent Application Nos. 61/563807, 61/563751, 61/563755, 61/563731, 61/56376761/563776, 61/563796, and 61/563828, which are all hereby incorporated by reference in their entireties.

Figure 37:
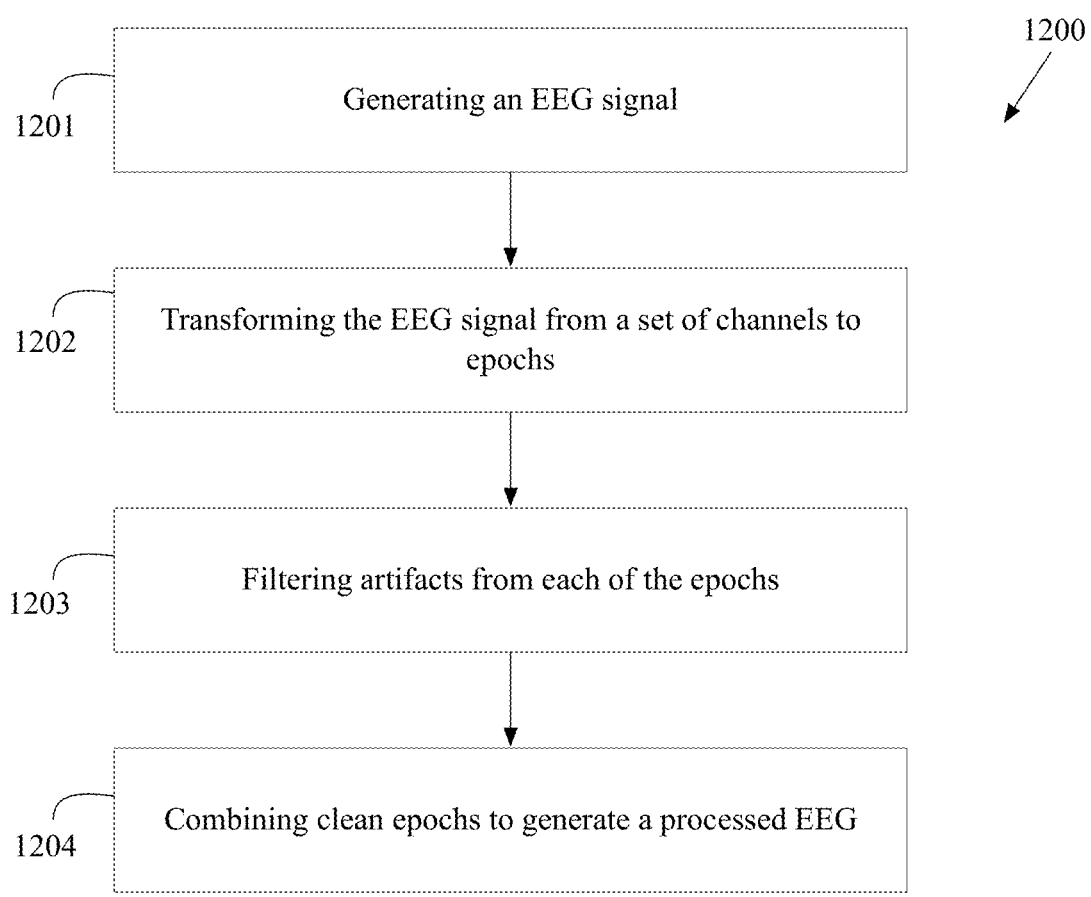
FIG. 37 is a flow chart of a general method for filtering artifacts from an EEG signal.

FIG. 37 is a flow chart of a general method 1200 for filtering artifacts from an EEG signal. At block 1201, an EEG signal is generated from a machine comprising a plurality of electrodes, an amplifier and processor. At block 1202, the EEG signal is transformed from a set of channels into a plurality of epochs. At block 1203, artifacts from each of the plurality of epochs are filtered using an artifact removal algorithm to generate a plurality of clean epochs. At block 1204, the clean epochs are combined to generate a processed EEG recording.

Each of the plurality of epochs has an epoch duration length of two seconds and an increment of one second. Alternatively, each of the plurality of epochs has an epoch duration length of four seconds and an increment of two seconds.

The artifact removal algorithm is preferably a blind source separation algorithm. The blind source separation algorithm is preferably a CCA algorithm or an ICA algorithm.

The clean epochs are preferably combined using a weighted average and the weight of the weighted average is preferably proportional to the ratio of the distance to an epoch center.

Figure 38:
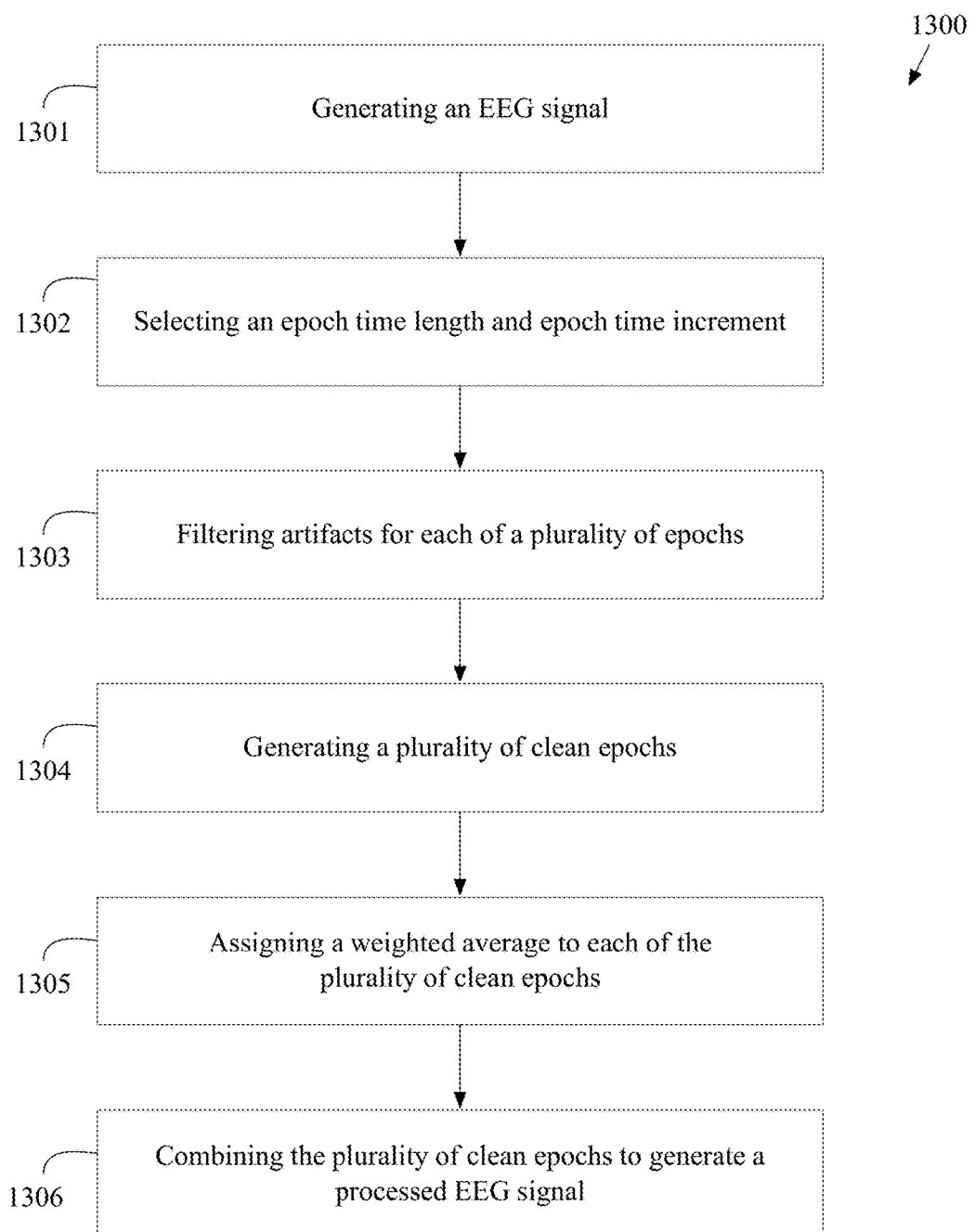
FIG. 38 is a flow chart of a specific method for filtering artifacts from an EEG signal.

FIG. 38 is a flow chart of a specific method 1300 for filtering artifacts from an EEG signal. At block 1301, an EEG signal is generated from a machine. At block 1302, an epoch time length and an epoch time increment are selected for the EEG signal. At block 1303, artifacts from each of the plurality of epochs are filtered using an artifact removal algorithm. At block 1304, a plurality of clean epochs is generated from the artifact removed epochs. At block 1305, a weighted average is assigned to each of the plurality of clean epochs. At block 1306, the clean epochs are combined to generate a processed EEG recording.

Each of the plurality of epochs has an epoch duration length of two seconds and an increment of one second. Alternatively, each of the plurality of epochs has an epoch duration length of four seconds and an increment of two seconds.

The artifact removal algorithm is preferably a blind source separation algorithm. The blind source separation algorithm is preferably a CCA algorithm or an ICA algorithm.

The clean epochs are preferably combined using a weighted average and the weight of the weighted average is preferably proportional to the ratio of the distance to an epoch center.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method for displaying electroencephalogram (EEG) data, the method comprising:

with a processor performing artifact reduction on an original EEG signal comprising a first plurality of channels to generate a processed continuous EEG report, the processed continuous EEG report comprising a second plurality of channels, wherein performing artifact reduction comprises partitioning the original EEG signal into a plurality of epochs, performing artifact reduction on the plurality of epochs to generate a plurality of artifact reduced epochs, and combining the plurality of artifact reduced epochs to generate a processed EEG recording, wherein each of the plurality of artifact reduced epochs overlaps an adjacent artifact reduced epoch to produce a continuous processed EEG recording without discontinuities in the processed EEG recording, wherein the plurality of artifact reduced epochs are combined using a weighted average wherein each of the plurality of artifact reduced epochs and the adjacent artifact reduced epoch are combined using a weighted average wherein the weight is proportional to a ratio of distances to epoch centers wherein a value from each of the plurality of artifact reduced epochs is weighted higher for an overlapping portion nearer a center of each of the plurality of artifact reduced epochs and a value from the adjacent artifact reduced epoch is weighted higher for an overlapping portion nearer a center of the artifact reduced epoch;

overlaying the processed continuous EEG report on the original EEG report to generate a combined EEG report, wherein an x-axis of the processed continuous EEG report is aligned with an x-axis of the original EEG report, wherein a y-axis of the processed continuous EEG report is aligned with a y-axis of the original EEG report; and displaying the combined EEG report on a display screen of a monitor, the monitor in communication with the processor, wherein the processed EEG report is visually distinctive from the original EEG report, wherein an activity at a specific time on one channel of the first plurality of channels of the original EEG report is identifiable on a corresponding channel of the second plurality of channels of the processed EEG report at the specific time, wherein the amplitudes of the signals for the original EEG report are contained within each of the plurality of first channels in order to prevent overlapping of the signals and the amplitudes of the signals for the processed EEG report are contained within each of the plurality of second channels in order to prevent overlapping of the signals.

2. The method according to claim 1 wherein the artifact reduction is for at least one of muscle artifact, eye movement artifact, electrical artifact, heartbeat artifact, tongue movement artifact, and chewing artifact.

3. The method according to claim 1 wherein the combined EEG report comprises the processed EEG report having a first color and the original EEG report having a second color different than the first color.

4. The method according to claim 1 wherein the combined EEG report comprises the processed EEG report having a first style and the original EEG report having a second style different than the first style.

5. The method according to claim 1 wherein the overlay of the processed EEG report on the original EEG report has the overlay of each channel of the second plurality of channels of the processed EEG report within each corresponding channel of the first plurality of channels of the original EEG report.

6. The method according to claim 1 further comprising switching from a display of the combined EEG report to a display of only the processed continuous EEG report.

7. The method according to claim 6 further comprising switching from the display of the processed continuous EEG report to a display of only the original EEG report.

* * * * *